US008609719B2

(12) United States Patent
Piryatinsky et al.

(10) Patent No.: US 8,609,719 B2
(45) Date of Patent: Dec. 17, 2013

(54) PROPARGYLATED AMINOINDANS, PROCESSES FOR PREPARATION, AND USES THEREOF

(75) Inventors: Victor Piryatinsky, Netanya (IL); Bronka Cohen, Netanya (IL); David Lerner, Jerusalem (IL); Dalia Pinkert, Kfar Saba (IL); Istvan Miskolczi, Debrecen-Pallag (HU); Yaacov Herzig, Ra'anana (IL); Hugo Gottlieb, Rehovot (IL); Marta Weinstock-Rosin, Jerusalem (IL)

(73) Assignees: Yissum Research Development Company of the Hebrew University of Jerusalem, Jerusalem (IL); Technion Research and Development Foundation Ltd., Haifa (IL)

( * ) Notice: Subject to any disclaimer, the term of this patent is extended or adjusted under 35 U.S.C. 154(b) by 279 days.

(21) Appl. No.: 12/582,491

(22) Filed: Oct. 20, 2009

(65) Prior Publication Data
US 2010/0093848 A1 Apr. 15, 2010

Related U.S. Application Data

(63) Continuation of application No. 11/710,118, filed on Feb. 23, 2007, now Pat. No. 7,625,946.

(60) Provisional application No. 60/776,386, filed on Feb. 24, 2006.

(51) Int. Cl.
*A61K 31/13* (2006.01)

(52) U.S. Cl.
USPC .......................................................... 514/480

(58) Field of Classification Search
None
See application file for complete search history.

(56) References Cited

U.S. PATENT DOCUMENTS

| | | | |
|---|---|---|---|
| 2,573,645 A | 10/1951 | Kerwin et al. |
| 2,916,490 A | 12/1959 | Schenck et al. |
| 2,982,783 A | 5/1961 | Schneck et al. |
| 3,060,091 A | 10/1962 | Witkin |
| 3,123,642 A | 3/1964 | Temple et al. |
| 3,178,478 A | 4/1965 | Huebner et al. |
| 3,201,470 A | 8/1965 | Huebner et al. |
| 3,253,037 A | 5/1966 | Huebner et al. |
| 3,308,157 A | 3/1967 | Robertson et al. |
| 3,507,962 A | 4/1970 | Taylor |
| 3,513,240 A | 5/1970 | Bernardus et al. |
| 3,513,244 A | 5/1970 | Gittos et al. |
| 3,637,740 A | 1/1972 | Sarges |
| 3,704,323 A | 11/1972 | Krapcho |
| 3,709,996 A | 1/1973 | Gittos et al. |
| 3,751,420 A | 8/1973 | Hauck et al. |
| 3,804,898 A | 4/1974 | Panneman |
| 3,886,168 A | 5/1975 | Himmele et al. |
| 3,903,297 A | 9/1975 | Robert |
| 3,991,207 A | 11/1976 | Sarges et al. |
| 4,029,731 A | 6/1977 | Sarges |
| 4,096,173 A | 6/1978 | Molloy |
| 4,128,666 A | 12/1978 | Bondinell et al. |
| 4,132,737 A | 1/1979 | Molloy |
| 4,134,997 A | 1/1979 | Cannon et al. |
| 4,172,093 A | 10/1979 | Göransson-Dahlander et al. |
| 4,632,939 A | 12/1986 | Beedle et al. |
| 4,638,001 A | 1/1987 | Kuhla et al. |
| 4,788,130 A | 11/1988 | Oshiro et al. |
| 4,792,628 A | 12/1988 | Oshiro et al. |
| 4,826,875 A | 5/1989 | Chiesi |
| 4,833,273 A | 5/1989 | Goel et al. |
| 4,873,241 A | 10/1989 | Napier et al. |
| 4,948,807 A | 8/1990 | Rosin et al. |
| 5,011,995 A | 4/1991 | Pugin et al. |
| 5,071,875 A | 12/1991 | Horn et al. |
| 5,118,704 A | 6/1992 | Minaskanian et al. |
| 5,134,147 A | 7/1992 | Peglion et al. |
| 5,153,225 A | 10/1992 | Schohe et al. |
| 5,189,045 A | 2/1993 | Peglion et al. |
| 5,196,583 A | 3/1993 | Yamada et al. |
| 5,225,596 A | 7/1993 | Carlsson et al. |
| 5,242,919 A | 9/1993 | Oshiro et al. |
| 5,273,974 A | 12/1993 | Goto et al. |
| 5,286,747 A | 2/1994 | Arvidsson et al. |
| 5,378,729 A | 1/1995 | Kohn et al. |
| 5,387,612 A | 2/1995 | Youdim et al. |
| 5,389,687 A | 2/1995 | Schaus et al. |

(Continued)

FOREIGN PATENT DOCUMENTS

EP 0 436 492 A2 7/1991
EP 0 538 134 B1 4/1993

(Continued)

OTHER PUBLICATIONS

Armstrong et al., "Acylation effects on chiral recognition of racemic amines and alcohols by new polar and non-polar cyclodextrin derivative gas chromatographic phases," J. Chromatography 502:154-159 (1990).
Askin et al., "Highly Diastereoselective Alkylations of Chiral Amide Enolates: New Routes to Hydroxyethylene Dipeptide Isostere Inhibitors of HIV-1 Protease," J. Org. Chem. 57:2771-2773 (1992).
Baker et al., "Synthesis of decahydrocyclopentacyclo-octene derivatives via intramolecular photocycloaddition of $A^{\alpha,\beta}$-butenolides and reductive cleavage," J. Chem. Soc., Chem. Commun. 23:1011-1012 (1980).
Barton et al., "Reductive Formylation of Oximes; An Approach to the Synthesis of Vinyl Isonitriles," Tetrahedron Letters 29(27):3343-3346 (1988).
Barker et al., "Principles of Ambulatory Medicine, Fourth Edition," Williams & Wilkins publishers, 4:1240-1257 (1995).

(Continued)

Primary Examiner — Yevegeny Valenrod
(74) Attorney, Agent, or Firm — Winston & Strawn LLP

(57) ABSTRACT

A method for treating an individual who has been identified as having Alzheimer's disease by administering orally to the individual a therapeutically effective amount of ladostigil or a pharmaceutically active salt thereof, wherein the therapeutically effective amount is 70 mg per day, 140 mg per day, or 200 mg per day. Also, a unit dosage form of ladostigil or a pharmaceutically active salt thereof in an amount of 50 mg, 70 mg, 80 mg or 100 mg.

10 Claims, No Drawings

(56) References Cited

U.S. PATENT DOCUMENTS

| | | |
|---|---|---|
| 5,401,758 A | 3/1995 | Atwal et al. |
| 5,453,446 A | 9/1995 | Youdim et al. |
| 5,457,133 A | 10/1995 | Youdim et al. |
| 5,486,541 A | 1/1996 | Sterling et al. |
| 5,516,943 A | 5/1996 | Gao et al. |
| 5,519,061 A | 5/1996 | Youdim et al. |
| 5,532,415 A | 7/1996 | Youdim et al. |
| 5,569,669 A | 10/1996 | Guillaumet et al. |
| 5,576,353 A | 11/1996 | Youdim et al. |
| 5,602,176 A | 2/1997 | Enz |
| 5,639,913 A | 6/1997 | Lidor et al. |
| 5,646,188 A | 7/1997 | Gilad et al. |
| 5,654,301 A | 8/1997 | Kohn et al. |
| 5,668,181 A | 9/1997 | Youdim et al. |
| 5,708,018 A | 1/1998 | Haadsma-Svensson et al. |
| 5,744,500 A | 4/1998 | Youdim et al. |
| 5,786,390 A | 7/1998 | Youdim et al. |
| 5,844,003 A | 12/1998 | Tatton et al. |
| 5,877,218 A | 3/1999 | Herzig et al. |
| 5,877,221 A | 3/1999 | Cohen et al. |
| 5,880,159 A | 3/1999 | Herzig et al. |
| 5,891,923 A | 4/1999 | Youdim et al. |
| 5,914,349 A | 6/1999 | Cohen et al. |
| 5,994,408 A | 11/1999 | Cohen et al. |
| 6,251,938 B1 | 6/2001 | Chorev et al. |
| 6,303,650 B1 | 10/2001 | Chorev et al. |
| 6,316,504 B1 | 11/2001 | Youdim et al. |
| 6,462,222 B1 | 10/2002 | Chorev et al. |
| 6,528,685 B2 | 3/2003 | Cohen et al. |
| 6,538,025 B2 | 3/2003 | Chorev et al. |
| RE39,616 E | 5/2007 | Chorev et al. |
| 2002/0142969 A1 | 10/2002 | Jeschke ............... 530/331 |
| 2004/0010038 A1 | 1/2004 | Blaugrund et al. |
| 2005/0065176 A1 | 3/2005 | Field ..................... 514/214 |
| 2005/0267077 A1 | 12/2005 | Gallagher ............. 514/750 |
| 2006/0189685 A1 | 8/2006 | Caciularu et al. |
| 2006/0189819 A1 | 8/2006 | Bahar |
| 2006/0276537 A1 | 12/2006 | Goren et al. |
| 2007/0135518 A1 | 6/2007 | Weinstock-Rosin |
| 2007/0203232 A1 | 8/2007 | Piryatinsky ............ 562/41 |
| 2007/0232691 A1 | 10/2007 | Goren |
| 2007/0293583 A1 | 12/2007 | Weinstock-Rosin ......... 514/484 |
| 2009/0131535 A1 | 5/2009 | Blaugrund ............. 514/657 |

FOREIGN PATENT DOCUMENTS

| | | |
|---|---|---|
| EP | 0 614 888 A1 | 9/1994 |
| EP | 0 664 291 A1 | 7/1995 |
| EP | 0 951 284 B1 | 10/1999 |
| GB | 852735 | 11/1960 |
| GB | 1003686 | 9/1965 |
| HK | 1022838 | 7/2004 |
| JP | 3-2155 A | 1/1991 |
| WO | WO 91/00724 A1 | 1/1991 |
| WO | WO 93/11761 A1 | 6/1993 |
| WO | WO 94/22495 A1 | 10/1994 |
| WO | WO 95/04027 A1 | 2/1995 |
| WO | WO 95/11016 A1 | 4/1995 |
| WO | WO 95/18617 | 7/1995 |
| WO | WO 96/02524 A1 | 2/1996 |
| WO | WO 96/37199 A1 | 11/1996 |
| WO | WO 97/07093 A1 | 2/1997 |
| WO | WO 97/12583 A2 | 4/1997 |
| WO | WO 98/02152 A1 | 1/1998 |
| WO | WO 98/26775 A1 | 6/1998 |
| WO | WO 98/27055 A1 | 6/1998 |
| WO | WO 03/072055 A2 | 9/2003 |
| WO | WO 2005/051371 | 6/2005 |
| WO | WO 2006/091656 A1 | 8/2006 |
| WO | WO 2006/091836 A1 | 8/2006 |
| WO | WO 2006/130726 A2 | 12/2006 |
| WO | WO 2007/070425 A2 | 6/2007 |
| WO | WO 2007/087029 A2 | 8/2007 |
| WO | WO 2007/100583 A2 | 9/2007 |

OTHER PUBLICATIONS

Bentue-Ferrer et al., "Monoamine Oxidase B Inhibitors," CNS Drugs 6(3):217-236 (1996).
Boar et al., "A Simple Synthesis of Enamides from Ketoximes," J. Chem. Soc., Perkins 1, pp. 1237-1241 (1975).
Boltshauser et al., "Vanishing white matter and ovarian dysgenesis in an infant with cerebro-oculo-facio-skeletal phenotype," Neuropediatrics 33(2):57-62 (2002).
Brettle et al., "Synthesis of Enamides," J. Chem. Soc., Perkin Trans. 1, pp. 2185-2195 (1988).
Burk et al., "A Three-Step Procedure for Asymmetric Catalytic Reductive Amidation of Ketones," J. Org. Chem. 63(18):6084-6085 (1998).
Chorvat et al., "Acetylcholine release enhancing agents: potential therapeutics for Alzheimer's disease," Drugs of the Future 20(11):1145-1162 (1995).
Chrisp et al., "Selegiline: A Review of its Pharmacology, Symptomatic Benefits and Protective Potential in Parkinson's Disease," Drugs & Aging 1(3):228-248 (1991).
Chumpradit et al., "Synthesis and Optical Resolution of (R)- and (S)-trans-7-Hydroxy-2-[N-propyl-N-(3'-iodo-2'-propenyl)amino]tetralin: A New D3 Dopamine Receptor Ligand," J. Med. Chem. 36:4308-4312 (1993).
Chumpradit et al., "Synthesis, resolution and radioiodination of S(-)trans-5-hydroxy-2-[N-n-propylN-(3'-iodo-2'-propenyl)amino]tetralin-S (-)trans-5-OH-PIPAT: A new dopamine D2-like receptor ligand," Journal of Labelled Compounds and Radiopharmaceuticals 36(11):1051-1062 (1995) (abstract only).
Cooper et al., "Alzheimer's Disease Drug Treatment," Journal of Geriatric Drug Therapy 8(2):5-18 (1993).
Cutler et al., "Muscarinic $M_1$-Receptor Agonists: Potential in the Treatment of Alzheimer's Disease," CNS Drugs 3(6):467-481 (1995).
Davis et al., "Tacrine," The Lancet 345:625-630 (1995).
Delgado et al., "Wilson and Gisvold's Textbook of Organic Medicinal and Pharmaceutical Chemistry, Ninth Edition," J.B. Lippincott Company publishers, (1995).
Dostert "Can our knowledge of monoamine oxidase (MAO) help in the design of better MAO inhibitors?," J Neural Transm 41:269-279 (1994).
Drefahl et al., "Amino alcohols. I. Cis- and trans-DL-1-amino-2-hydroxytetrahydronaphthalene and cis- and trans-DL-1-amino-2-hydroxyindan," Che. Abstract 52:16417f (1958).
Drefahl et al., "Amino Alcohols. X. Addition of iodine isocyanate to unsymmetrical olefins," Che. Abstracts 54:13078f (1960).
Dutta et al., "Synthesis and Characterization of Novel Derivatives of 2-Aminotetralins: Development of Highly Selective Derivatives for the D3 Receptor," Medicinal Chemistry Research 10(4):208-229 (2000).
Finberg et al., "Modification of blood pressure and nictitating membrane response to sympathetic amines by selective monoamine oxidase inhibitors, types A and B, in the cat," Br J Pharmacol. 85(2):541-546 (1985).
Fink et al., "Imino 1,2,3,4-tetrahydrocyclopent[b]indole carbamates as dual inhibitors of acetylcholinesterase and monoamine oxidase," Bioorganic & Medicinal Chemistry Letters 6(6):625-630 (1996).
Fitton et al., "Moclobemide: A Review of its Pharmacological Properties and Therapeutic Use in Depressive Illness," Drugs 43(4):561-596 (1992).
Florvall et al., "Prodrugs of neuron-selective monoamine oxidase inhibitors• amino acid derivatives of 1-(4-aminophenyl)-2-aminopropanes," Eur. J. Med. Chem 34:137-151 (1999).
Fuller et al , "Inhibition in vitro of norepinephrine N-methyltransferase by 2-aminotetralins, analogs of phenylethylamines with rigid conformation," Biochem Pharmacol. 26(5):446-447 (1976).
Gabryel et al., "Nootropics: pharmacological properties and therapeutic use," Pol J Pharmacol. 46(5):383-394 (1994).
Ghislandi et al., "Scissione Ottica E Configurazione Dell'1-Aminobenzociclobutene E Dell'1-Aminoindano," Boll. Chim Farm. 115:489-500 (1976).
Harvey, "The Pharmacology of Galanthamine and its Analogues," Pharmac. Ther. 68(1):113-128 (1995).

(56) References Cited

OTHER PUBLICATIONS

Hazelhoff et al., "N-methyl,N-propargyl-2-aminotetralins: Novel dopamine agonists with monoamine oxidase inhibiting properties," European Journal of Pharmacology 109(2):229-240 (1985).

Hazelhoff et al., "The neuropharmacological profile of N-methyl-N-propargyl-2-aminotetralin: a potent monoamine oxidase inhibitor," Naunyn-Schmiedeberg's Arch Pharmacol 330:50-58 (1985).

Heikkila et al., "Prevention of MPTP-induced neurotoxicity by AGN-1133 and AGN-1135, selective inhibitors of monoamine oxidase-B," European Journal of Pharmacology 116(3):313-317 (1985).

Hori et al., "N-containing diphenylethylamine derivatives and acid adducts", Japan Kokai Tokyo Koho JP 54-132559, Oct. 15, 1979, Database CAPLUS on STN®, Chemical Abstracts Service, (Columbus, Ohio), Accession No. 1980:180807, abstract.

Horn et al., "Brain Levels and Metabolism of the Dopaminergic Agonist 2-Amino-6,7-dihydroxytetrahydronaphthaline After Administration of Various Prodrugs," J. Med. Chem. 25(8):993-996 (1982).

Horn et al., "Steric Requirements for Catecholamine Uptake by Rat Brain Synaptosomes: Studies with Rigid Analogs of Amphetamine," Journal of Pharmacology and Experimental Therapeutics 180(3):523-530 (1972).

Huebner, "1-(N-Methyl-N-propargylamino)indans and related compounds," Chem. Abstracts 61:3046a (1964).

Jovan et al., "A retrospective chart review of risperidone use in treatment-resistant children and adolescents with psychiatric disorders," Progress in Neuro-Psychopharmacology and Biological Psychiatry 26(2):267-275 (2002).

Kabins et al., "Potential Applications for Monoamine Oxidase B Inhibitors," Dementia 1:323-348 (1990).

Kametani et al., "Studies on the Syntheses of Heterocyclic Compounds. CLIX. The Reaction of 2-Nitro-1-indanone Oxime with Formalin and Hydrochloric Acid," Chem. Pharm. Bull. 14(12):1408-1413 (1966).

Knapp et al., "A 30-Week Randomized Controlled Trial of High-Dose Tacrine in Patients with Alzheimer's Disease," JAMA 271(13):985-991 (1994).

Kragten et al., "Glyceraldehyde-3-phosphate Dehydrogenase, the Putative Target of the Antiapoptotic Compounds CGP 3466 andR-(—)-Deprenyl," The Journal of Biological Chemistry 273(10):5821-5828 (1998).

Laso et al., "A New Selective Reduction of Nitroalkenes into Enamides," Tetrahedron Letters 37(10):1605-1608 (1996).

Lidor et al., "A Facile Synthesis for Racemic and Optically Active 1-Aminoindans," Organic Preparations and Procedures International (OPPI) 29(6):701-706 (1997).

Löscher et al , "Inhibition of Monoamine Oxidase Type A, but Not Type B, is an Effective Means of Inducing Anticonvulsant Activity in the Kindling Model of Epilepsy," Journal of Pharmacology and Experimental Therapeutics 288(3):984-992 (1999).

Martin et al., "Potential Anti-Parkinson Drugs Designed by Receptor Mapping," J Med Chem 16(2):147-150 (1973).

Martin et al., "Discriminant Analysis of the Relationship between Physical Properties and the Inhibition of Monoamine Oxidase by Aminotetralins and Aminoindans," J Med Chem 17(4):409-413 (1974).

Mealy et al., "Drugs of the Future," 29(3):293 (2004), Accession No. 2004176769.

Mouna et al., "Enantioselective Acetylation of Primary Amines by Cylindrocarpon Radiciola," Bioorg. Med. Chem. Lett. 3(4):681-684 (1993).

Nakamura, "Aniracetam: its novel therapeutic potential in cerebral dysfunctional disorders based on recent pharmacological discoveries," CNS Drug Rev. 8(1):70-89 (2002).

Nakanishi et al., "Preparation of Enamides via Reductive Acylation of N-Acetoxyimino Compounds by Use of $Fe_3(CO)_{12}$," Chemistry Letters 16(11):2167-2168 (1987).

O'Malley et al., "Synthesis and Biological Evaluation of Combined Acetyl Cholinesterase (AChE) and Monoamine Oxidase (MAO) Inhibitors," 205th ACS Mtg. (MEDI), abstract 78 (1993).

Oshiro et al., "Novel Cerebroprotective Agents with Central Nervous System Stimulating Activity. 1. Synthesis and Pharmacology of 1-Amino-7-Hydroxyindan Derivatives," J Med Chem 34(7):2004-2013 (1991).

Palermo et al., "Combined Acetylcholinesterase (AChE) and Reversible Monoamine Oxidase (MAO) Inhibition as Potential Therapeutic Approach for Senile Dementia of the Alzheimer Type (SADT)," 205th ACS Mtg. (MEDI), abstract 77 (1993).

Palfreyman et al , "Inhibition of Monoamine Oxidase Selectively in Brain Monoamine Nerves Using the Bioprecursor (E-β-Fluoromethylene-m-Tyrosine (MDL 72394), a Substrate for Aromatic L-Amino Acid Decarboxylase," Journal of Neurochemistry 45(6):1850-1860 (1985).

Riederer et al., "Monoamine Oxidase Activity and Monoamine Metabolism in Brains of Parkinsonian Patients Treated with 1-Deprenyl," Journal of Neurochemistry 46(5):1359-1365 (1986).

Ruschig et al., "Preparation of 17α-hydroxy-20-keto steroids from 17(20)-en-20-acetamino steroids," Chem. Ber. 88(6):883-894 (1955).

Semerci et al., "Cerebro-oculo-facio-skeletal syndrome: report of two cases from Turkey with postmortem findings," Turkish Journal of Pediatrics 44(3):269-273 (2002).

Silverman, "The Organic Chemistry of Drug Design and Drug Action," pp. 15-20 (1992).

Singh et al., "Antimalarials. 7-Chloro-4-(substituted amino)quinolines," J Med Chem 14(4):283-286 (1971).

Smith et al., "Quality Improvement of Painful Peripheral Neuropathy," Seminars in Oncology Nursing 18(1):36-43 (2002).

Speiser et al., "Effect of chronic treatment with ladostigil (TV-3326) on anxiogenic and depressive-like behaviour and on activity of the hypothalamic-pituitary-adrenal axis in male and female prenatally stressed rats," Pharmacology (Berl), Apr. 14, 2005 (abstract).

Sramek et al., "Safety/Tolerability Trial of SDZ ENA 713 in patients with Probable Alzheimer's Disease," Life Sciences 58(15):1201-1207 (1996).

Sterling et al., "Novel Dual Inhibitors of AChE and MAO Derived from Hydroxy Aminoindan and Phenethylamine as Potential Treatment for Alzheimer's Disease," J Med Chem 45(24):5260-5279 (2002).

Tariot et al., "Treatment of Alzheimer's Disease: Gilmmers of Hope?" Chemistry and Industry 20:801-803, 806-807 (1993).

Tekes et al., "Effect of MAO Inhibitors on the Uptake and Metabolism of Dopamine in Rat and Human Brain," Pol J Pharmacol Pharm. 40(6):653-658 (1988).

Teranishi et al., "Facile Synthesis of 6-Hydroxyindole and 6-Methoxyindole via Regioselective Friedel-Crafts Acylation and Baeyer-Villiger Oxidation," Synthesis 10:1018-1020 (1994).

Terni et al., "Preparation of (aminoalkyl)phenyl morpholinoalkylcarbamates and analogs as cholinesterase inhibitors," WO 96/02524, Feb. 1, 1996, Database CAPLUS on STN®, Chemical abstracts Service (Columbus, Ohio), Accesion No. 1996:340192, abstract.

Thoene et al., "Physicians' Guide to Rare Diseases," Dowden Publishing Company, Inc., Montvale, N.J., pp. 55, 56, 285-288, 215-217, 329-340, 352-355, 359, 361, 395, 396, 456-45440:4396-4405 (1992).

Top et al., "N-Alkylation of Nitriles with Tricarbonylchromium Complexes of Benzyl and Related Alcohols as Synthetic Intermediates. Further Development of the Ritter Reactions," J. Chem. Soc., Chem. Commun. 224-225 (1979).

Weinstock, "The Pharmacotherapy of Alzheimer's Disease Based on the Cholinergic Hypothesis: an Update," Neurodegeneration 4:349-356 (1995).

White et al., "Mechanism of Monoamine Oxidase-A Inhibition by BW 1370U87," Drug Development Research 25:191-199 (1992).

Yavich et al., "The interaction of L-deprenyl and scopolamine on spatial learning/memory in rats," Journal of Neural Transmission: Parkinson's Disease and Dementia Section 6(3):189-197 (1993).

(56) References Cited

OTHER PUBLICATIONS

Youdim et al., "Momamine Oxidase," Handbook of Experimental Pharmacology vol. 90/I, Tredelenburg and Weiner, eds., Springer-Verlag, London: Chapter 3, pp. 119-192.
Youdim et al., "Rasagiline: Neurodegeneration, Neuroprotection, and Mitochondrial Permeability Transition," Journal of Neuroscience Research 79:172-179 (2005).
Zheng et al., "Asymmetric Synthesis of α-Amino Acid Derivatives via an Electrophilic Amination of Chiral Amide Cuprates with Li t-Butyl-N-Tosyloxycarbamate," Tetrahedron Letters 38(16):2817-2820 (1997).
Zhu et al., "Asymmetric Rh-Catalyzed Hydrogenation of Enamides with a Chiral 1,4-Bisphosphine Bearing Diphenylphosphino Groups," J. Org. Chem. 63:9590-9593 (1998).
"Agent for Cognition Disorders Acetylcholinesterase Inhibitor," Drugs of the Future 16(1):16-18 (1991).
"Cognition Enhancer Acetylcholinesterase Inhibitor," E-2020, Drugs of the Future 20(1):77-78 (1995).
"Cognition Enhancer Acetylecholinesterase Inhibitor," TAK-147, Drugs of the Future 20(3):248-250 (1995).
"The Merck Index, an Encyclopedia of Chemicals, Drugs, and Biologicals," Tenth Edition, Windholz et al., eds., Merck & Co. Inc., Rahway, N.J., pp. 149, 248-249 (1983).
"The Merck Manual of Diagnosis and Therapy," Fifteenth Edition, vol. 1, Berkow et al., eds., Merck Sharp & Dohme Research Laboratories, Rahway, N.J., pp. 1030-1033 (1987).
"The Merck Manual of Diagnosis and Therapy," Fifteenth Edition, vol. 1, Berkow et al., eds., Merck Sharp & Dohme Research Laboratories, Rahway, N.J., pp. 1054-1055 (1987).
"Effect of Deprenyl on the Progression of Disability in Early Parkinson's Disease," The Parkinson Study Group, The New England Journal of Medicine 321(20):1364 (1989).
"Effects of Tocopherol and Deprenyl on the Progression of Disability in Early Parkinson's Disease," The Parkinson Study Group, The New England Journal of Medicine 328(3):176-183 (1993).
Chemical Abstracts Service (Columbus, Ohio) Registry No. 209394-46-7.
Hungarian patent No. HU 9802316 (corresponds to WO 97/07093 and U.S. patent publication No. 2002/0142969).
Japanese patent No. 54132559, Caplus Abstract, Apr. 1978.
Supplementary European Search Report, application No. EP 03716197.3 (Sep. 25, 2007).
International Search Report, application No. PCT/US2006/006251 (May 22, 2006).
International Preliminary Report on Patentability, application No. PCT/US2006/006251 (Aug. 28, 2007).
International Preliminary Examination Report, application No. PCT/US03/05871 (Apr. 26, 2004).
International Preliminary Examination Report, application No. PCT/US97/23897 (Dec. 5, 1998).
International Search Report, application No. PCT/US03/05871 (Aug. 21, 2003).
International Search Report, application No. PCT/US06/006636 (Dec. 27, 2006).
International Search Report, application No. PCT/US06/21182 (Nov. 2, 2006).
Arnaiz, E. et al., (2001) Impaired cerebral glucose metabolism and cognitive functioning predict deterioration in mild cognitive impairment. Neuroreport 12(4):851-5.
Bartolini, L. et al., (1996) Aniracetam restores object recognition impaired by age, scopolamine, and nucleus basalis lesions. Pharmacol Biochem Behav. 53(2):277-83.
Bolanos, Juan P. et al., (2004) Regulation of glucose metabolism by nitrosative stress in neural cells. Mol Aspects Med. 25(1-2):61-73.
Buccafusco, J. J. et al., (2003) Potential Cognitive actions, of (N-Propargly -(3R)-aminoindan -5-yl)-ethyl, methyl carbamate (TV3326), a novel neuroprotective agent, as assessed in old Rhesus monkeys in their performance of versions of a delayed matching task. Neuroscience 119:669-678.

Casu, Maria Antonietta et al., (2002) Aging causes a preferential loss of cholinergic innervation of characterized neocortical pyramidal neurons. Cereb Cortex 12(3):329-337.
Chen, Yun et al., (1998) Cerebro-protective effects of ENA713, a novel acetylcholinesterase inhibitor, in closed head injury in the rat. *Brain Research* 784:18-24.
Chen, Yun et al., (1998) Rivastigmine, a brain-selective acetylcholinesterase inhibitor, ameliorates cognitive and motor deficits induced by closed-head injury in the mouse. Journal of Neurotrauma 15(4):231-237.
Ellmann, George L. et al., (1961) A new and rapid colorimetric determination of acetylcholinesterase activity. Biochem Pharmacol 7(2):88-95.
Feldman, Howard H. et al., (2007) Effect of rivastigmine on delay to diagnosis of Alzheimer's disease from mild cognitive impairment: the InDDEx study. Lancet Neurology 6(6):501-512.
Finch, Caleb E. (2003) Neurons, glia, and plasticity in normal brain aging. Neurobiol. Aging 24:S123-7.
Good, Paul F. et al., (1996) Evidence of neuronal oxidative damage in Alzheimer's disease. Am J Pathol. 149(1):21-8.
Gordon, Christopher J. (1994) Thermoregulation in laboratory mammals and humans exposed to anti- cholinesterase agents. Neurotoxicol. Teratol. 16(5):427-453.
Griffin, W. S. T. et al., (1998) Glial-neuronal interactions in Alzheimer's disease: the potential role of a 'cytokine cycle' in disease progression. Brain Pathol. 8(1):65-72.
Hensley, K. et al., In "Neuroinflammation: mechanisms and management" (Ed: P. L. Wood), Humana Press Inc., 1997.
Kielian, Tammy and Esen, Nilufer (2004) Effects of neuroinflammation on glia-glia gap junctional intercellular communication: a perspective. Neurochem Int. 45(2-3):429-36.
Lannert, Heinrich and Hoyer, Siegfried (1998) Intracerebroventricular administration of streptozotocin causes long-term diminutions in learning and memory abilities and in cerebral energy metabolism in adult rats. Behav Neurosci.112(5):1199-1208.
Lipton, Stuart A. and Rosenbrg, Paul A.(1994) Excitatory amino acids as a final common pathway for neurological disorders N Engl J Med. 330(9):613-22.
Maruyama, Wakako et al., (2003) Anti-apoptotic action of anti-Alzheimer drug, TV3326 [(N-propargyl)-(3R)-aminoindant-5-yl]-ethyl methyl carbamate, a novel cholinesterase-monoamine oxidase inhibitor. Neurosci Lett. 341(3):233-236.
Mattson, Mark P. et al., (1997) Activation of NF-κB protects hippocampal neurons against oxidative stress-induced apoptosis: Evidence for induction of manganese superoxide dismutase and suppression of peroxynitrite production and protein tyrosine nitration. J Neurosci Res. 49(6):681-697.
McCarty, Mark F. (2006) Down-regulation of microglial activation may represent a practical strategy for combating neurodegenerative disorders. Med Hypotheses 67(2):251-269.
McGeer, Edith G. and McGeer, Patick L. (2003) Inflammatory processes in Alzheimer's disease. Prog. Neuro-Psychopharmacol. Biol. Psychiatry 27(5):741-9.
Meyer, John Stirling et al., (2005) MRI Abnormalities Associated with Mild Cognitive Impairments of Vascular (VMCI) Versus Neurodegenerative (NMCI) Types Prodromal for Vascular and Alzheimer's Dementias. Curr Alz Res 2(5):579-585.
Miguel-Hidalgo, J. J. et al., (2002) Neuroprotection by memantine against neurodegeneration induced by beta-amyloid (1-40), Brain Res. 958(1):210-221.
Moriera, P. I. et al., (2005) Oxidative stress mechanisms and potential therapeutics in Alzheimer disease. J Neural Transmission 112(7):921-932.
Mumby, Dave G. et al., (2002) Hippocampal damage and exploratory preferences in rats: memory for objects, places, and contexts. Learn Mem. 9(2):49-57.
Nitch, R. et al., (1989) The intracerebroventricularly streptozotocin-treated rat: impairment of cerebral glucose metabolism resembles the alterations of carbohydrate metabolism of the brain in Alzheimer's disease, J. Neural Transco. P-D sect 1(1-2):109-10.
Ouyang, Yi-Bing and Giffard, Rona G. (2004) Changes in astrocyte mitochondrial function with stress: effects of Bcl-2 family proteins. Neurochem Int. 45(2-3):371-9.

(56) References Cited

OTHER PUBLICATIONS

Parikh, "Granulation growth mechanisms and granulation characteristics", Handbook of pharmaceutical granulation technology, 1997 pp. 160-165.

Petersen, Ronald C. et al., (1999) Mild cognitive impairment. Clinical characterization and outcome. Arch Neurol 56(3):303-308 Erratum: (1999) Arch Neurol 56(6):760.

Petersen, Ronald C. et al., (2001) Current concepts in mild cognitive impairment. Arch Neurol. 58(12):1985-92.

Poltyrev, Tatyana et al., (2005) Effect of chronic treatment with ladostigil (TV-3326) on anxiogenic and depressive-like behaviour and on activity of the hypothalamic-pituitary-adrenal axis in male and female prenatally stressed rats. Psychopharmacology (Berl) 181(1):118-25 Epub Oct. 15, 2005.

Rosen, Wilma G. et al., (1984) A new rating scale for Alzheimer's disease. Am J Psychiatry 141:1356-1364.

Sagi, Yotam et al., (2003) Attenuation of MPTP-induced dopaminergic neurotoxicity by TV3326, a cholinesterase-monoamine oxidase inhibitor. J Neurochem. 86:290-297.

Sagi, Yotam et al., (2005) The neurochemical and behavioural effects of the novel cholinesterase-monoamine oxidase inhibitor, ladostigil, in response to L-dopa and L-tryptophan, in rats. Br J Pharmacol. 146(4):553-60.

Scali, C. et al., (2002) Effect of subchronic administration of metrifonate, rivastigmine and donepezil on brain acetylcholine in aged F344 rats. J. Neural Transm. 109(7-8):1067-1080.

Sharma, Monisha and Gupta, Y. K. (2001) Effect of chronic treatment of melatonin on learning, memory and oxidative deficiencies induced by intracerebroventricular streptozotocin in rats. Pharmacol Biochem Behav 70(2-3):325-331.

Sharma, Monish and Gupta, Y. K. (2002) Chronic treatment with trans resveratrol prevents intracerebroventricular streptozotocin induced cognitive impairment and oxidative stress in rats. Life Sci 71(21):2489-2498.

Shoham, S. et al., (2003) Intracerebroventricular injection of streptozotocin causes neurotoxicity to myelin that contributes to spatial memory deficits in rats. Exp Neurol. 184(2):1043-52.

Shoham, Shai et al., (2007) Ladostigil prevents gliosis, oxidative-nitrative stress and memory deficits induced by intracerebroventricular injection of streptozotocin in rats. Neuropharmacol 52(3):836-843.

Shytle, R. Douglas et al., (2004) Cholinergic modulation of microglial activation by alpha 7 nicotinic receptors. J Neurochem. 89(2):337-43.

Simmons, Martha L. and Murphy, Sean (1992) Induction of nitric oxide synthase in glial cells. J Neurochem. 59(3):897-905.

Takasu, N. et al., (1991) Streptozocin- and alloxan-induced H2O2 generation and DNA fragmentation in pancreatic islets. H2O2 as mediator for DNA fragmentation. Diabetes. 40(9):1141-5.

Takuma, Kazuhiro et al., (2004) Astrocyte apoptosis: implications for neuroprotection. Prog Neurobiol. 72(2):111-127.

Turrini, P. et al., (2001) Cholinergic nerve terminals establish classical synapses in the rat cerebral cortex: synaptic pattern and age-related atrophy. Neurosci. 105(2):277-285.

Tyurin, Vladimir A. et al., (2000) Oxidative stress following traumatic brain injury in rats: quantitation of biomarkers and detection of free radical intermediates. Journal of Neurochemistry 75(5):2178-2189.

Wahlgren, N. G. In R. Green, "International Review of Neurobiology: Neuroprotective Agents and Cerebral Ischemia", vol. 40, Academic Press, 1997.

Wang, R. H. et al., (2000) Gender differences in the effect of rivastigmine on brain cholinesterase activity and cognitive function in rats. Neuropharmacology 39(3):497-506.

Weinstock, M. et al., (2000) TV3326, a novel neuroprotective drug with cholinesterase and monoamine oxidase inhibitory activities for the treatment of Alzheimer's disease. J Neural Transm. Suppl. 60:157-69.

Weinstock, M. et al., (2000) Development of a novel neuroprotective drug (TV3326) for the treatment of Alzheimer's disease, with cholinesterase and monoamine oxidase inhibitory activities. Drug Dev. Res. 50: 216-222.

Weinstock, Marta et al., (2001) Neuroprotective Effects of Novel Cholinesterase Inhibitors Derived from Rasagiline as Potential Anti-Alzheimer Drugs. Ann. N.Y. Acad. Sci. 939:148-161.

Weinstock, M. et al., (2002) Limited potentiation of blood pressure response to oral tyramine by brain-selective monoamine oxidase A-B inhibitor, TV-3326 in conscious rabbits. Neuropharmacology 43(6):999-1005.

Weinstock, Marta et al., (2002) Effect of TV3326, a novel monoamine-oxidase cholinesterase inhibitor, in rat models of anxiety and depression, Psychopharmacology. 160(3):318-24.

Weinstock, M. et al., (2003) A novel cholinesterase and brain-selective monoamine oxidase inhibitor for the treatment of dementia comorbid with depression and Parkinson's disease. Prog. Neuropsychopharmacol. Biol. Psychiatry 27: 555-561.

Weinstock, M. et al., (2005) Ladostigil attenuates glicolisis and prevents oxidative-nitrative stress in hippocampus and memory deficits induced in rats by intracerebroventricular injection of streptozotocin. Reviews in the Neurosciences, Tel-Aviv, Israel16(suppl):S67.

Weinstock, M. and Shoham, S. (2004) Rat models of dementia based on reductions in regional glucose metabolism, cerebral blood flow and cytochrome oxidase activity. J Neural Trans. 111(3):347-366.

Winters, et al., (2004) Double dissociation between the effects of peri-postrhinal cortex and hippocampal lesions on tests of object recognition and spatial memory: heterogeneity of function within the temporal lobe, J. Neuroscience 24:5901-8.

Yogev-Falach, Merav et al., (2002) Involvement of MAP kinase in the regulation of amyloid precursor protein processing by novel cholinesterase inhibitors derived from rasagiline. FASEB 16:1674-1676.

Yogev-Falach, Merav et al., (2006) a multifunctional, neuroprotective drug, ladostigil (TV3326), regulates holo-APP translation and processing. FASEB 20:E1610-E1618.

Youdim, Moussa B. H. and Weinstock, Marta (2001) Molecular Basis of Neuroprotective Activities of Rasagiline and the Anti-Alzheimer Drug TV3326 [Ipar;N-Propargyl-(3R) Aminoindan-5-YL)-Ethyl Methyl Carbamate] Cell Mol Neurobiol. 21(6):555-73.

Youdim, Moussa B. H. and Weinstock, Marta (2002) Novel neuroprotective anti-Alzheimer drugs with anti-depressant activity derived from the anti-Parkinson drug, rasagiline. Mechanisms of Ageing and Development 123 (2002) 1081-1086.

Youdim, Moussa B. H. and Weinstock, Marta (2004) Therapeutic applications of selective and non-selective inhibitors of monoamine oxidase A and B that do not cause significant Tyramine potentiation. Neurotoxicology 25:243-250.

Youdim, Moussa B. H. et al., (2003) Amyloid processing and signal transduction properties of antiparkinson—antialzheimer neuroprotective drugs Rasagiline and TV3326. Ann. N.Y. Acad Sci 993:378-386.

Guidance for Industry: Estimating the Maximum Safe Starting Dose in Initial Clinical Trials for Therapeutics in Adult Healthy Volunteers, U.S. Dept. HHS/FDA/CDER (Jul. 2005), at http://www.fda.gov/cder/guidance/5541fnl.doc.

Handbook of Pharmaceutical Exipients. Published by the Pharmaceutical Press and the American Pharmacist Association. Fourth edition (2003). Edited by Rowe, Raymond C. et al., pp. 188, 430, 449, 705, 725-6, 737-8, 767.

Intelihealth, "Alzheimer's disease," online accessed Jun. 30, 2008, http://www.intelihealth.com/IH/intlh/WSIHW000/8303/9117/195703.html?d=dmtHealthAZ.

Intelihealth, "Dementia", online, accessed Sep. 22, 2009, http://wvvw.intelihealth.com/IH/intlh/WSIHW000/24479/11184.html.

Intelihealth, "Parkinson's disease", online accessed Sep. 22, 2009, http://www.intelihealth.conn/IH/intlH?d=dmtHealthAZ&c=201957.

Physician's Desk Reference (2005) $59^{th}$ edition. Publisher: Charles E. Baker, Jr. pp. 1583-5.

Rubin, Harold (2006) Mild Cognitive Impairment-Alzheimer's part XVI e-published on www.therubins.com Nov. 14, 2006.

(56) References Cited

OTHER PUBLICATIONS

"USP and NF excipients" The United States Pharmacopeia and The National Formulary, 2004, pp. 2809-2812.
U.S. Appl. No. 11/637,600 Requirement for restriction election dated May 7, 2009.
U.S. Appl. No. 11/637,600 Non-Final Rejection dated Oct. 15, 2009.
U.S. Appl. No. 11/635,922 Requirement for restriction/election May 13, 2009.
U.S. Appl. No. 11/635,922 Non-final rejection Oct. 15, 2009.
U.S. Appl. No. 11/635,922 Final rejection Jun. 8, 2010.
U.S. Appl. No. 11/637,600 Final rejection Jan. 19, 2011.
U.S. Appl. No. 11/637,600 Non-final rejection Oct. 15, 2009.
U.S. Appl. No. 11/637,600 Non-final rejection Jun. 9, 2010.
U.S. Appl. No. 11/361,379 Requirement for restriction/election May 14, 2008.
U.S. Appl. No. 11/361,379 Non-final rejection Oct. 30, 2008.
U.S. Appl. No. 11/361,379 Final rejection Apr. 15, 2010.
U.S. Appl. No. 11/361,379 Advisory Action Jun. 30, 2010.
U.S. Appl. No. 11/361,379 Non-final rejection Aug. 3, 2010.
ISR of PCT/US2006/047038 mailed Dec. 11, 2007.
IPRP of PCT/US2006/047038 mailed Dec. 11, 2007.
U.S. Appl. No. 60/656,866, of Bahar, Eliezer, filed Feb. 24, 2005.
U.S. Appl. No. 60/686,791, of Goren, Tamar filed Jun. 1, 2005.
U.S. Appl. No. 60/700,850, of Goren, Tamar filed Jul. 19, 2005.
U.S. Appl. No. 60/776,386, of Piryatinsky, Victor, filed Feb. 24, 2006.
U.S. Appl. No. 13/211,721, of Licht, Daniella, filed Aug. 17, 2011.

PROPARGYLATED AMINOINDANS, PROCESSES FOR PREPARATION, AND USES THEREOF

CROSS-REFERENCE TO RELATED APPLICATIONS

This application is a continuation of U.S. application Ser. No. 11/710,118 filed Feb. 23, 2007, now U.S. Pat. No. 7,625,946, which claims the benefit of Provisional Application No. 60/776,386, filed Feb. 24, 2006, the contents of each of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

PCT International Application Publication No. WO 98/27055 (U.S. Pat. No. 6,303,650, issued Oct. 16, 2001 to Chorev) discloses molecules of general formula I:

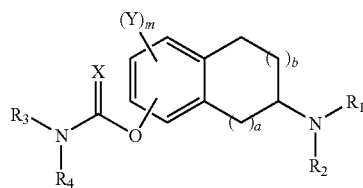

wherein when a is 0, b is 1 or 2; when a is 1, b is 1, m is from 0-3, X is O or S, Y is halogeno, $R_1$ is hydrogen or $C_{1-4}$ alkyl, $R_2$ is hydrogen, $C_{1-4}$ alkyl, or optionally substituted propargyl and $R_3$ and $R_4$ are each independently hydrogen, $C_{1-8}$ alkyl, $C_{6-12}$ aryl, $C_{6-12}$ aralkyl, each optionally substituted. These compounds have been disclosed as monoamine oxidase inhibitors that additionally inhibit acetylcholinesterase, and are useful to treat depression, Attention Deficit Disorder ("ADD"), Attention Deficit and Hyperactivity Disorder ("ADHD"), Tourett's Syndrome, Alzheimer's Disease and other dementias such as senile dementia, dementia of the Parkinson's type, vascular dementia and Lewy body dementia.

One of the compounds disclosed in WO 98/27055 is R(+)-6-(N-methyl, N-ethyl-carbamoyloxy)-N'-propargyl-1-aminoindan, also known as (3R)-3-(prop-2-ynylamino)-2,3-dihydro-1H-inden-5-yl ethyl methyl carbamate (compound 76 in Table 5). In addition, salts are disclosed, including the ½ L-tartrate salt. This salt has been given the nonproprietary name ladostigil tartrate. Its CAS registry number is 209394-46-7. Disclosed herein are novel related compounds.

SUMMARY OF THE INVENTION

The subject invention provides a pharmaceutical composition comprising a compound having the structure:

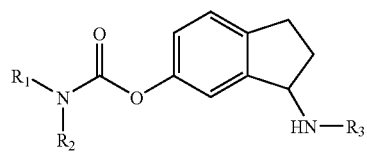

wherein $R_1$ is methyl and $R_2$ is H, or $R_1$ is ethyl and $R_2$ is hydroxymethyl; and
$R_3$ is H or propargyl; or
an enantiomer or a pharmaceutically acceptable salt thereof; and a pharmaceutically acceptable carrier.

The subject invention also provides a method of treating a subject afflicted with a psychiatric disorder, Parkinson's disease, Alzheimer's disease, dementia, or a neurological disorder comprising administering to the subject a therapeutically effective amount of a compound having the structure:

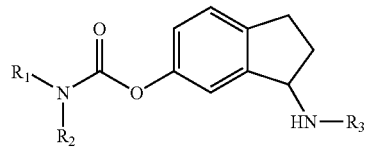

wherein $R_1$ is methyl and $R_2$ is H, or $R_1$ is ethyl and $R_2$ is hydroxymethyl; and
$R_3$ is H or propargyl; or
an enantiomer or a pharmaceutically acceptable salt thereof.

The subject invention also provides a process for making a compound having the structure:

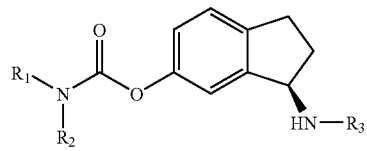

wherein $R_1$ is methyl and $R_2$ is H, or $R_1$ is ethyl and $R_2$ is hydroxymethyl; and
$R_3$ is H or propargyl;
comprising administering to a human subject an amount of R(+)-6-(N-methyl, N-ethyl-carbamoyloxy)-N'-propargyl-1-aminoindan, or a pharmaceutically acceptable salt thereof.

The subject invention also provides a process for making a compound having the structure:

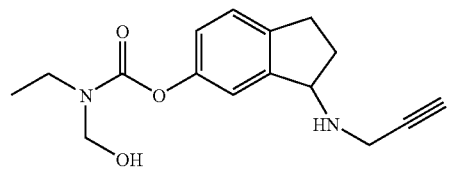 [SMILES: C#CCNC1CCc2ccc(OC(=O)N(CC)CO)cc21]

comprising
a) reacting a compound having the structure:

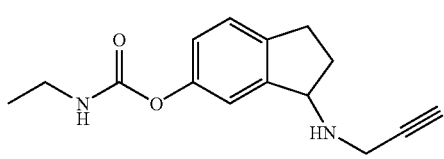 [SMILES: C#CCNC1CCc2ccc(OC(=O)NCC)cc21]

or a salt thereof with paraformaldehyde and water so as to make the compound, and
b) recovering the compound from the reaction mixture.

The subject invention also provides a process for making a compound having the structure:

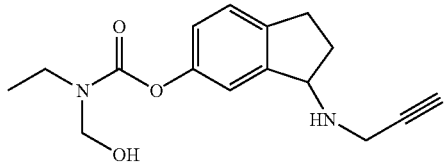 [SMILES: C#CCNC1CCc2ccc(OC(=O)N(CC)CO)cc21]

comprising
a) reacting a compound having the structure:

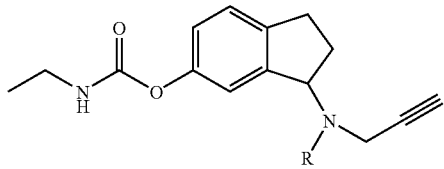

wherein R is a protecting group,
with paraformaldehyde and water in an organic solvent in the presence of an acidic moiety so as to produce a product;
b) reacting the product of step a) with an acidifying agent so as to thereby remove the protecting group and make the compound; and
c) recovering the compound made in step b).

The subject invention also provides a process for making a compound having the structure:

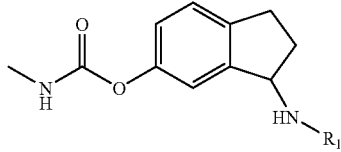

wherein $R_1$ is H or propargyl, comprising
a) reacting a compound having the structure:

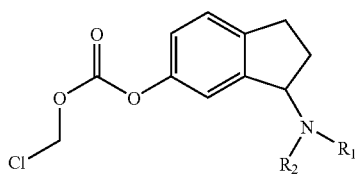

wherein $R_1$ is H or propargyl and $R_2$ is a protecting group, with methylamine to form a product having the structure:

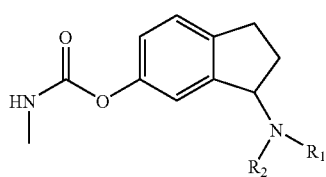

b) reacting the product formed in step a) with an acidifying agent so as to make the compound; and
c) recovering the compound made in step b).

The subject invention provides an isolated compound having the structure:

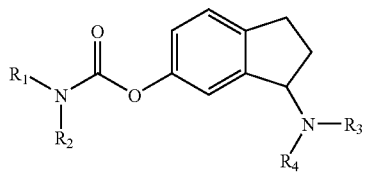

wherein $R_1$ is methyl and $R_2$ is H, or $R_1$ is ethyl and $R_2$ is hydroxymethyl;
$R_3$ is H or propargyl; and
$R_4$ is either H or t-butyloxycarbonyl; or
an enantiomer or a pharmaceutically acceptable salt thereof.

The subject invention also provides a method for assaying the amount of ethyl-hydroxymethyl-carbamic acid 3-R-(prop-2-ynylamino)-indan-5-yl ester in a sample comprising the steps:
a) obtaining a sample; and
b) determining the amount of ethyl-hydroxymethyl-carbamic acid 3-(prop-2-ynylamino)-indan-5-yl ester in the sample.

The subject invention also provides a method for assaying the amount of methyl-carbamic acid 3-R-amino-indan-5-yl ester in a sample comprising the steps:
a) obtaining a sample; and
b) determining the amount of methyl-carbamic acid 3-R-amino-indan-5-yl ester in the sample.

The subject invention also provides a method for assaying the amount of methyl-carbamic acid 3-(prop-2-ynylamino)-indan-5-yl ester in a comprising the steps:
a) obtaining a sample; and
b) determining the amount of methyl-carbamic acid 3-(prop-2-ynylamino)-indan-5-yl ester in the sample.

The subject invention also provides a use of a compound having the structure:

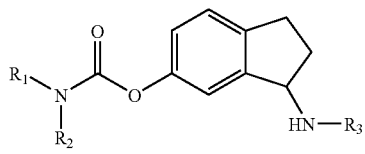

wherein $R_1$ is methyl and $R_2$ is H, or $R_1$ is ethyl and $R_2$ is hydroxymethyl; and
$R_3$ is H or propargyl; or
an enantiomer or a pharmaceutically acceptable salt thereof, for the preparation of a medicament for treating a subject afflicted with a psychiatric disorder, Parkinson's disease, Alzheimer's disease, dementia, or a neurological disorder.

DETAILED DESCRIPTION OF THE INVENTION

The subject invention provides a pharmaceutical composition comprising a compound having the structure:

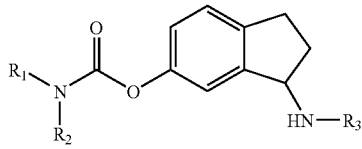

wherein $R_1$ is methyl and $R_2$ is H, or $R_1$ is ethyl and $R_2$ is hydroxymethyl; and $R_3$ is H or propargyl; or an enantiomer or a pharmaceutically acceptable salt thereof; and a pharmaceutically acceptable carrier. The pharmaceutical composition can comprise any one of the specific compounds described herein.

In an embodiment of the pharmaceutical composition, the compound has the structure:

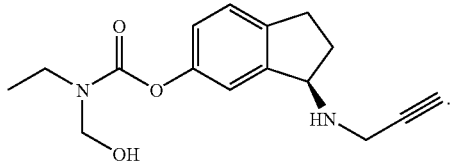 [SMILES: C#CCN[C@@H]1CCc2ccc(OC(=O)N(CC)CO)cc21 ; "."]

In another embodiment of the pharmaceutical composition, the compound has the structure:

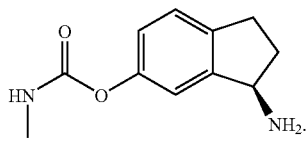

In another embodiment of the pharmaceutical composition, the compound has the structure:

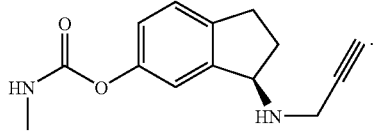

In another embodiment of the pharmaceutical composition the form of the composition is a solid.

The subject invention also provides a method of treating a subject afflicted with a psychiatric disorder, Parkinson's disease, Alzheimer's disease, dementia, or a neurological disorder comprising administering to the subject a therapeutically effective amount of a compound having the structure:

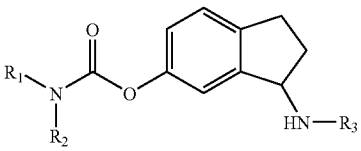

wherein $R_1$ is methyl and $R_2$ is H, or $R_1$ is ethyl and $R_2$ is hydroxymethyl; and $R_3$ is H or propargyl; or an enantiomer or a pharmaceutically acceptable salt thereof.

In an embodiment of the method the subject is afflicted with a psychiatric disorder.

In another embodiment of the method the psychiatric disorder may be depression, generalized anxiety disorder, obsessive-compulsive disorder, panic attacks and panic disorder, phobic disorder, stress disorder, depersonalized disorder, dissociative amnesia, dissociative fugue, dissociative identity disorder, personality disorder, delusional disorder, schizoaffective disorder, schizophrenia, schizophreniform disorder, substance-induced psychotic disorder, gender identity disorder, paraphilias, body dysmorphic disorder, hypochondriasis, Munchausen's syndrome, pain disorder, or somatization disorder.

Depression is an illness that involves the body, mood and thoughts and comes in a variety of types, including, major depression, dysthymia and bipolar disorder. Major depression is manifested by a combination of symptoms that interfere with the ability to work, study, sleep, eat, and enjoy pleasurable activities. Such a disabling episode of depression may occur only once but more commonly occurs several times in a lifetime. Dysthymia is a less severe type of depression involving long-term, chronic symptoms that do not disable a person, but prevent one from functioning well or feeling good. Another type of depression is bipolar disorder (manic-depressive illness). It is not as common as other depressive disorders. Individuals with bipolar disorder experience cycling mood changes involving severe highs (mania) and lows (depression). Depressive disorders are primarily treated medically with selective serotonin reuptake inhibitors (SSRIs) and monoamine oxidase inhibitors (MAOIs). (National Institute of Mental Health, "Depression" 2002)

In an embodiment of the method, the subject is afflicted with a neurological disorder.

In another embodiment of the method the neurological disorder may be epilepsy, narcolepsy, amyotrophic lateral sclerosis ("ALS"), memory disorders, panic, post-traumatic stress disorder ("PTSD"), sexual dysfunction, attention deficit and hyperactivity syndrome ("ADHD"), attention deficit disorder, or Tourette's syndrome.

In another embodiment of the method, the subject is afflicted with dementia.

In another embodiment the dementia may be static dementia, Alzheimer's-type dementia, senile dementia, presenile dementia, progressive dementia, vascular dementia or Lewy body dementia.

In another embodiment of the method, the subject is afflicted with Alzheimer's disease.

In another embodiment of the method, the subject is afflicted with Parkinson's disease.

In another embodiment of the method, the subject is afflicted with depression.

In yet another embodiment of the method, the compound has the structure:

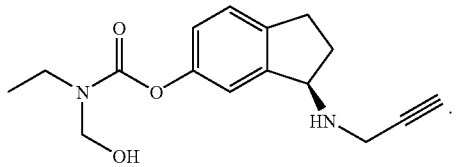

In yet another embodiment of the method, the compound has the structure:

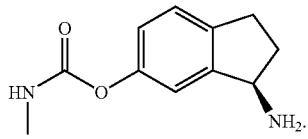

In yet another embodiment of the method, the compound has the structure:

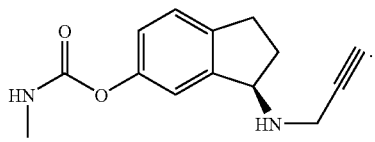 [SMILES: C#CCN[C@@H]1CCc2ccc(OC(=O)NC)cc21 ; "."]

The subject invention also provides a process for making a compound having the structure:

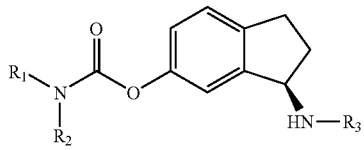

wherein $R_1$ is methyl and $R_2$ is H, or $R_1$ is ethyl and $R_2$ is hydroxymethyl; and
$R_3$ is H or propargyl;
comprising administering to a human subject an amount of R(+)-6-(N-methyl, N-ethyl-carbamoyloxy)-N'-propargyl-1-aminoindan, or a pharmaceutically acceptable salt thereof.

Although the compound can be recovered from the subject, production of the compound in the subject may be the goal. This process can be used to produce any one of the specific compounds described herein by the selection of appropriate starting materials. In an embodiment of the process, the compound administered to the human subject is R(+)-6-(N-methyl, N-ethyl-carbamoyloxy)-N'-propargyl-1-aminoindan ½ tartrate.

The subject invention also provides a process for making a compound having the structure:

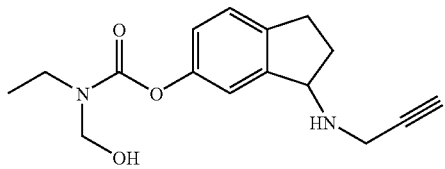 [SMILES: C#CCNC1CCc2ccc(OC(=O)N(CC)CO)cc21]

comprising
a) reacting a compound having the structure

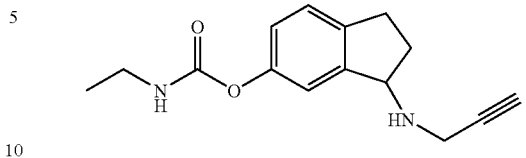

or a salt thereof with paraformaldehyde and water so as to make the compound, and
b) recovering the compound from the reaction mixture.

The compound produced by this process can be any one of the compounds described herein, including ethyl-hydroxymethyl-carbamic acid 3-R-(prop-2-ynylamino)-indan-5-yl ester, methyl-carbamic acid 3-R-amino-indan-5-yl ester or methyl-carbamic acid 3-R-(prop-2-ynylamino)-indan-5-yl ester.

In an embodiment of the process, the reaction of step a) is performed in the presence of an acidifying agent.

In another embodiment of the process, the acidifying agent is HCl, acetic acid, or a cation exchange resin.

In yet another embodiment of the process, recovery in step b) is performed using chromatography, extraction or flash column chromatography.

The subject invention also provides a process for making a compound having the structure:

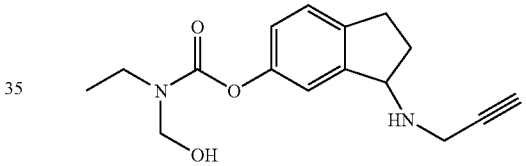

comprising
a) reacting a compound having the structure

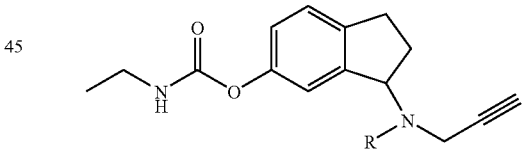

wherein R is a protecting group,
with paraformaldehyde and water in an organic solvent in the presence of an acidic moiety so as to produce a product;
b) reacting the product of step a) with an acidifying agent so as to thereby remove the protecting group and make the compound; and
c) recovering the compound made in step b).

In specific embodiments of the process, the acidic moiety can be HCl or a cation exchange resin, or the HCl anion of the starting material of step a), as exemplified in Example 3d, infra.

In an embodiment of the process, the protecting group is t-butyloxycarbonyl.

In another embodiment of the process, the organic solvent is dioxane or tetrahydrofuran.

In yet another embodiment of the process, the acidifying agent is HCl in ethyl acetate.

The subject invention also provides a process for making a compound having the structure:

[Structure: methyl carbamate of 3-aminoindan with NH-R₁]

wherein R₁ is H or propargyl, comprising
a) reacting a compound having the structure

[Structure: chloromethyl carbonate of indanol with N(R₁)(R₂)]

wherein R₁ is H or propargyl and R₂ is a protecting group, with methylamine to form a produce having the structure

[Structure: methyl carbamate of indanol with N(R₁)(R₂)]

b) reacting the product formed in step a) with an acidifying agent to make the compound; and
c) recovering the compound made in step b).

In an embodiment of the process, R₂ is t-butyloxycarbonyl.
In another embodiment of the process, the acidifying agent is HCl in ethyl acetate.
In yet another embodiment of the process, prior to step a) a compound of having the structure:

[Structure: 5-hydroxyindan with N(R₁)(R₂)]

wherein R₁ is H or propargyl and R₂ is a protecting group, is reacted with chloromethyl chloroformate to produce the compound as which the reaction of step a) is performed.

The subject invention provides an isolated compound having the structure:

[Structure: carbamate of indanol with R₁,R₂ on one N and R₃,R₄ on the other]

wherein R₁ is methyl and R₂ is H, or R₁ is ethyl and R₂ is hydroxymethyl;

R₃ is H or propargyl; and
R₄ is either H or t-butyloxycarbonyl; or
an enantiomer or a pharmaceutically acceptable salt thereof.

In an embodiment of the compound, R₄ is H.
In another embodiment, the compound has the structure:

[Structure: ethyl-hydroxymethyl-carbamic acid 3-(prop-2-ynylamino)-indan-5-yl ester]

or
an enantiomer or a pharmaceutically acceptable salt thereof.
In another embodiment, the compound is ethyl-hydroxymethyl-carbamic acid 3-(prop-2-ynylamino)-indan-5-yl ester fumarate (2:1).
In another embodiment, the compound is ethyl-hydroxymethyl-carbamic acid 3-R-(prop-2-ynylamino)-indan-5-yl ester, or a pharmaceutically acceptable salt thereof.
In another embodiment, the compound is ethyl-hydroxymethyl-carbamic acid 3-R-(prop-2-ynylamino)-indan-5-yl ester fumarate (2:1).
In yet another embodiment, the compound has the structure:

[Structure: methyl-carbamic acid 3-amino-indan-5-yl ester]

or
an enantiomer or a pharmaceutically acceptable salt thereof.
In yet another embodiment, the compound is methyl-carbamic acid 3-amino-indan-5-yl ester hydrochloride.
In yet another embodiment, the compound is methyl-carbamic acid 3-R-amino-indan-5-yl ester, or a pharmaceutically acceptable salt thereof.
In yet another embodiment, the compound is methyl-carbamic acid 3-R-amino-indan-5-yl ester hydrochloride.
In a further embodiment, the compound has the structure:

[Structure: methyl-carbamic acid 3-(prop-2-ynylamino)-indan-5-yl ester]

or
an enantiomer or a pharmaceutically acceptable salt thereof.
In a further embodiment, the compound is methyl-carbamic acid 3-(prop-2-ynylamino)-indan-5-yl ester hydrochloride.
In a further embodiment, the compound is methyl-carbamic acid 3-R-(prop-2-ynylamino)-indan-5-yl ester, or a pharmaceutically acceptable salt thereof.
In a further embodiment, the compound is methyl-carbamic acid 3-R-(prop-2-ynylamino)-indan-5-yl ester hydrochloride.

In yet a further embodiment, the compound has the structure:

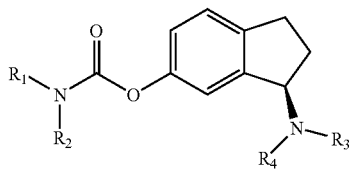

wherein $R_4$ is t-butyloxycarbonyl.

In yet a further embodiment of the compound, $R_1$ is methyl, $R_2$ is H, and $R_3$ is propargyl.

In yet a further embodiment of the compound, $R_1$ is methyl, $R_2$ is H, and $R_3$ is H.

In yet a further embodiment of the compound, $R_1$ is ethyl, $R_2$ is hydroxymethyl, and $R_3$ is propargyl.

The subject invention also provides a method for assaying the amount of ethyl-hydroxymethyl-carbamic acid 3-R-(prop-2-ynylamino)-indan-5-yl ester in a sample comprising the steps:
a) obtaining a sample; and
b) determining the amount of ethyl-hydroxymethyl-carbamic acid 3-(prop-2-ynylamino)-indan-5-yl ester in the sample.

The subject invention also provides a method for assaying the amount of methyl-carbamic acid 3-R-amino-indan-5-yl ester in a sample comprising the steps:
a) obtaining a sample; and
b) determining the amount of methyl-carbamic acid 3-R-amino-indan-5-yl ester in the sample.

The subject invention also provides a method for assaying the amount of methyl-carbamic acid 3-(prop-2-ynylamino)-indan-5-yl ester in a sample comprising the steps:
a) obtaining a sample; and
b) determining the amount of methyl-carbamic acid 3-(prop-2-ynylamino)-indan-5-yl ester in the sample.

The subject invention also provides use of a compound having the structure:

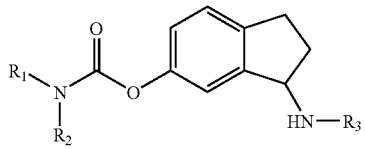

wherein $R_1$ is methyl and $R_2$ is H, or $R_1$ is ethyl and $R_2$ is hydroxymethyl; and
$R_3$ is H or propargyl; or
an enantiomer or a pharmaceutically acceptable salt thereof, for the preparation of a medicament for treating a subject afflicted with a psychiatric disorder, Parkinson's disease, Alzheimer's disease, dementia, or a neurological disorder.

In an embodiment of the use, the subject is afflicted with a psychiatric disorder.

In another embodiment of the use the psychiatric disorder may be depression, generalized anxiety disorder, obsessive-compulsive disorder, panic attacks and panic disorder, phobic disorder, stress disorder, depersonalized disorder, dissociative amnesia, dissociative fugue, dissociative identity disorder, personality disorder, delusional disorder, schizoaffective disorder, schizophrenia, schizophreniform disorder, substance-induced psychotic disorder, gender identity disorder, paraphilias, body dysmorphic disorder, hypochondriasis, Munchausen's syndrome, pain disorder, or somatization disorder.

In an embodiment of the use, the subject is afflicted with a neurological disorder.

In another embodiment of the use, the neurological disorder is epilepsy, narcolepsy, amyotrophic lateral sclerosis ("ALS"), memory disorders, panic, post-traumatic stress disorder ("PTSD"), sexual dysfunction, attention deficit and hyperactivity syndrome ("ADHD"), attention deficit disorder, or Tourette's syndrome.

In another embodiment of the use, the subject is afflicted with dementia.

In another embodiment of the use dementia is static dementia, Alzheimer's-type dementia, senile dementia, pre-senile dementia, progressive dementia, vascular dementia or Lewy body dementia.

In another embodiment of the use, the subject is afflicted with Alzheimer's disease.

In another embodiment of the use, the subject is afflicted with Parkinson's disease.

In another embodiment of the use, the subject is afflicted with depression.

In yet another embodiment of the use, the compound has the structure:

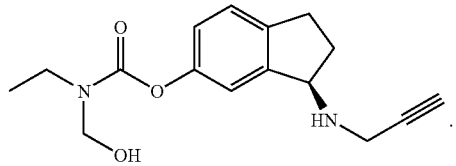 [SMILES: C#CCN[C@@H]1CCc2ccc(OC(=O)N(CC)CO)cc21 ; "."]

In yet another embodiment of the use, the compound has the structure:

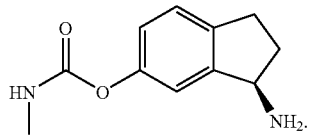

In yet another embodiment of the use, the compound has the structure:

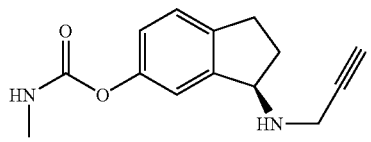

The enzyme monoamine oxidase ("MAO") plays an essential role in the metabolic degradation of important amine neurotransmitters including dopamine, serotonin and noradrenaline. Thus, agents that inhibit MAO are of potential therapeutic benefit for a variety of neurological disease indications, including Parkinson's disease, Alzheimer's disease, depression, epilepsy, narcolepsy, amyotrophic lateral sclerosis ("ALS"), etc. (Szelnyi, I.; Bentue-Ferrer et al.; Loscher et al.; White et al.; U.S. Pat. No. 5,744,500).

Acetylcholinesterase ("AChE") inhibition is a route implicated in certain neurological disorders, but is a different route from the route of MAO inhibition.

The disclosed compounds are both MAO inhibitors and AChE inhibitors.

The compounds of the present invention may be prepared as pharmaceutical compositions. Such compositions may comprise the compound and/or pharmaceutically acceptable salts thereof, together with pharmaceutically acceptable carriers and/or excipients. Pharmaceutically acceptable salts include, but are not limited to, the mesylate, maleate, fumarate, tartrate, hydrochloride, hydrobromide, esylate, p-toluenesulfonate, benzoate, acetate, phosphate and sulfate salts.

The compositions may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art.

Specific examples of pharmaceutical acceptable carriers and excipients that may be used to formulate oral dosage forms of the present invention are described, e.g., in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

As used herein, an "isolated" compound is a compound that is separate from the mixture of components normally found in or excreted by an animal, for example a human, such as cells, organs, blood, saliva, urine, etc. Thus, an isolated compound is not part of the mixture which constitutes animal, blood, saliva, urine, etc., nor is it part of an animal cell or organ. An isolated compound may be obtained by separation from the animal, or, alternatively, by a chemical synthesis process.

As used herein, a "pharmaceutically acceptable" carrier is one that is suitable for use with humans and/or animals without undue adverse side effects (such as toxicity, irritation, and allergic response) commensurate with a reasonable benefit/risk ratio, and is not blood or blood plasma.

EXAMPLES

Experimental Details

Example 1

Preparation of ethyl-carbamic acid 3-R-(N-Boc-prop-2-ynylamino)-indan-5-yl ester Ethyl-carbamic acid 3-R-(prop-2-ynylamino)-indan-5-yl ester HCl was prepared as described in U.S. Pat. No. 6,303,650 (compound 56 in table 5) using the R-enantiomer starting material. Ethyl-carbamic acid 3-R-prop-2-ynylamino-indan-5-yl ester HCl (0.5 g, 1.70 mmol) was converted to its free base by dissolving it in a mixture of water (20 ml), 30% ammonium hydroxide (20 ml), and dichloromethane (30 ml). The layers were separated, and the aqueous layer was re-extracted with dichloromethane (8×30 ml). The combined organic layers were dried ($Na_2SO_4$), and evaporated to dryness at reduced pressure to give 400 mg of the free base as a viscous oil. The free base (0.40 g, 1.55 mmol) was dissolved in absolute ethanol (20 ml), and a solution of di-tert-butyl dicarbonate (0.35 g, 1.60 mmol) in ethanol (10 ml) was added. The mixture was stirred at 25° C. under nitrogen for 24 h, and the solvent was removed at reduced pressure. Hexane (50 ml) was added to the residue, the mixture was stirred at room temperature for 30 min, and the hexane was decanted off. The hexane washing and decanting steps were repeated (5×30 ml), and the combined hexane washings were evaporated to dryness at reduced pressure. The residue was dried under vacuum for 24 h to give 550 mg (90%) of the title compound as an off-white solid.

Example 2

Preparation of ethyl-hydroxymethyl-carbamic acid 3-R-(N-Boc-prop-2-ynylamino)-indan-5-yl ester A mixture of ethyl-carbamic acid 3-R-(N-Boc-prop-2-ynylamino)-indan-5-yl ester prepared in Example 1 (1.08 g, 3 mmol), paraformaldehyde (180 mg, 6 mmol), pretreated Lewatit SPC 108 (a polystyrene sulfonic acid cation exchange resin,) (180 mg, 0.75 mequiv. of $H^+$), dioxane (6 ml), and water (21.6 mg, 1.2 mmol) was stirred and heated at 60° C. under nitrogen for 24 hr. The mixture was cooled to 25° C. and filtered. The residue on the filter was washed with dioxane, and the filtrate was evaporated to dryness at reduced pressure. The crude residue which resulted after evaporation of the dioxane was purified by flash column chromatography (elution with ethyl acetate/hexane 70/30) to give 450 mg (38% yield) of the title compound as a viscous oil.

$^{13}$C-NMR (CD$_3$CN) δ 14.19 and 15.03 (MeCH$_2$), 28.45 (Me$_3$C), 30.30 (C-2), 31.37 (C-1), 34.11 and 35.42 (NCH$_2$CCH), 42.40 and 42.62 (MeCH$_2$), 62.21 and 63.71 (C-3), 72.01 and 72.30 (NCH$_2$OH, NCH$_2$CCH), 80.95 (Me$_3$C), 82.48 (NCH$_2$CCH), 118.30 (C-4), 122.34 (C-6), 126.22 (C-7), 141.44 (C-3a), 151.43 (C-5), 155.80 (NCO).

Example 3a

Preparation of ethyl-hydroxymethyl-carbamic acid 3-R-prop-2-ynylamino-indan-5-yl ester A solution of ethyl-hydroxymethyl-carbamic acid 3-R-(N-Boc-prop-2-ynylamino)-indan-5-yl ester prepared in Example 2 (150 mg, 0.386 mmol) and 2N HCl in ethyl acetate (20 ml, 40 mmol) was stirred at room temperature for 2 hr. The mixture was evaporated to dryness at reduced pressure, and the residue was treated with water (10 ml), dichloromethane (20 ml), and enough 5% sodium bicarbonate solution to bring the pH of the aqueous layer to 8.5-9.0. The layers were separated, and the aqueous layer was re-extracted with dichloromethane (4×15 ml). The organic layers were combined and evaporated to dryness to give 90 mg of a viscous oil. Purification by flash column chromatography gave 11 mg (9%) of the title compound (free base) (90% pure by NMR).

Example 3b

Preparation of ethyl-hydroxymethyl-carbamic acid 3-R-(prop-2-ynylamino)-indan-5-yl ester A mixture of ethyl-carbamic acid 3-R-(prop-2-ynylamino)-indan-5-yl ester HCl salt (5.0 g, 16.96 mmol), water (41.5 ml), paraformaldehyde (2.03 g, 67.6 mmol), and 1N HCl (9 ml, 9.0 mmol) was stirred and heated in a glass stoppered flask at 37-40° C. for 7 hours. The mixture was cooled in an ice bath, and water (40 ml) and dichloromethane (60 ml) were added. Saturated sodium bicarbonate (enough to bring the pH to 8.5-9.0) was added slowly while stirring. The two layers were separated, and the aqueous layer was re-extracted with dichloromethane (7×40 ml). The organic layers were combined, dried (sodium sulfate), filtered, and evaporated to dryness at 25° C. under vacuum to give 5.0 g of crude ethyl-hydroxymethyl-carbamic acid 3-R-(prop-2-ynylamino)-indan-5-yl ester as a white solid. This was stored in the freezer until purified by flash column chromatography as detailed below.

The eluting solution (3% EtOH/CHCl$_3$+NH$_3$) was prepared as follows:

A mixture of CHCl$_3$ (800 ml) and 25% NH$_4$OH (40 ml) was placed in a 1 L separatory funnel, shaken vigorously, left to stand (tightly sealed) for 1 hr, and the phases separated. Most of the organic phase (about 750 ml) was collected in an Erlenmeyer flask containing NaSO$_4$ (40 g), and the mixture filtered rapidly (gravitationally, through a cotton-filled funnel) into a measuring cylinder, to give about 720 ml of ammoniacal chloroform solution (pH=10), which was then transferred into a tightly sealed bottle. The appropriate amount of EtOH was then added to give the required 3% v/v solution.

A solution of crude ethyl-hydroxymethyl-carbamic acid 3-R-(prop-2-ynylamino)-indan-5-yl ester free base (5 g) in minimum amount of CHCl$_3$ was charged on a 4.5 cm wide column filled (35 cm height) with silica previously wetted with the above solution. Ethyl-hydroxymethyl-carbamic acid 3-R-(prop-2-ynylamino)-indan-5-yl ester was eluted by the same solution and monitored by TLC (run in the same medium and detected by UV plus ninhydrin), to give 3.3 g of a viscous colorless oil (68%) containing about 7% CHCl$_3$ (w/w, by NMR).

Spectral and analytical data of ethyl-hydroxymethyl-carbamic acid 3-R-(prop-2-ynylamino)-indan-5-yl ester:

$^1$H-NMR (CD$_3$CN, δ):

Major Rotamer:

1.18 (brt, J=7 Hz, 3H, MeCH$_2$), 1.82 (m, 1H, H-2), 2.40 (m, 1H, H-2), 2.45 (t, J=2.5 Hz, 1H, NCH$_2$CCH), 2.77 (brdt, J=15.5, 7 Hz, 1H, H-1), 2.94 (ddd, J=15.5, 8, 5 Hz, 1H, H-1), 3.40 (m, 2H, MeCH$_2$), 3.44 (m, 2H, NCH$_2$CCH), 4.31 (t, J=6.5 Hz, 1H, H-3), 4.88 (brs, 2H, NCH2OH), 6.92 (dd, J=8, 2 Hz, 1H, H-6), 7.04 (d, J=2 Hz, 1H, H-4), 7.21 (d, J=8 Hz, 1H, H-7) ppm.

Minor Rotamer:

1.26 (brt, J=7 Hz, 3H, MeCH$_2$), 1.82 (m, 1H, H-2), 2.40 (m, 1H, H-2), 2.45 (t, J=2.5 Hz, 1H, NCH$_2$CCH), 2.77 (brdt, J=15.5, 7 Hz, 1H, H-1), 2.94 (ddd, J=15.5, 8, 5 Hz, 1H, H-1), 3.44 (m, 2H, NCH$_2$CCH), 3.50 (m, 2H, MeCH$_2$), 4.31 (t, J=6.5 Hz, 1H, H-3), 4.78 (brs, 2H, NCH$_2$OH), 6.92 (dd, J=8, 2 Hz, 1H, H-6), 7.04 (d, J=2 Hz, 1H, H-4), 7.21 (d, J=8 Hz, 1H, H-7) ppm.

$^{13}$C-NMR (CD$_3$CN, δ):

Major Rotamer:

14.26 (MeCH$_2$), 30.53 (C-2), 34.62 (C-1), 36.65 (NCH$_2$CCH), 42.69 (MeCH$_2$), 62.87 (C-3), 72.07 (NCH$_2$OH), 72.35 (NCH$_2$CCH), 83.78 (NCH$_2$CCH), 118.83 (C-4), 121.99 (C-6), 126.03 (C-7), 141.74 (C-3a), 147.61 (C-7a), 151.21 (C-5) ppm.

Minor Rotamer:

15.09 (MeCH$_2$), 30.53 (C-2), 34.62 (C-1), 36.65 (NCH$_2$CCH), 42.44 (MeCH$_2$), 62.87 (C-3), 72.35 (NCH$_2$OH and NCH$_2$CCH), 83.78 (NCH$_2$CCH), 118.83 (C-4), 121.99 (C-6), 126.03 (C-7), 141.74 (C-3a), 147.61 (C-7a), 151.21 (C-5) ppm.

MS: 289 (MH$^+$, 12.17), 234 (100), 216 (29.64), 133 (92.66).

Example 3c

Preparation of ethyl-hydroxymethyl-carbamic acid 3-R-(prop-2-ynylamino)-indan-5-yl ester A mixture of ethyl-carbamic acid 3-R-(prop-2-ynylamino)-indan-5-yl ester free base (80 mg, 0.31 mmol), water (0.8 ml), paraformaldehyde (40 mg, 4 eq), and AcOH (36 μl, 2 eq) was stirred and heated in a glass stoppered flask at 37-40° C. for 48 hr. Water (1 ml) and paraformaldehyde (30 mg) were added and the mixture stirred at the same temperature for additional 24 hr, at which point LC/UV analysis indicated about 50% of ethyl-hydroxymethyl-carbamic acid 3-R-(prop-2-ynylamino)-indan-5-yl ester (the rest being mostly starting ethyl-carbamic acid 3-R-(prop-2-ynylamino)-indan-5-yl ester.

Example 3d

Preparation of ethyl-hydroxymethyl-carbamic acid 3-R-(prop-2-ynylamino)-indan-5-yl ester A mixture of ethyl-carbamic acid 3-R-(prop-2-ynylamino)-indan-5-yl ester HCl salt (50 mg, 0.17 mmol), water (0.41 ml, 22.8 mmol) and paraformaldehyde (20.3 mg, 0.67 mmol) was stirred at 40° C. for 48 hours. HPLC of the reaction mixture indicated 63% of ethyl-hydroxymethyl-carbamic acid 3-R-(prop-2-ynylamino)-indan-5-yl ester (plus 24% of ethyl-carbamic acid 3-R-(prop-2-ynylamino)-indan-5-yl ester).

Example 3e

Preparation of ethyl-hydroxymethyl-carbamic acid 3-R-(prop-2-ynylamino)-indan-5-yl ester A mixture of ethyl-carbamic acid 3-R-(prop-2-ynylamino)-indan-5-yl ester HCl (223 mg, 0.75 mmol), paraformaldehyde (45 mg, 1.5 mmol), pretreated Lewatit SPC 108 (a polystyrene sulfonic acid cation exchange resin,) (45 mg, 0.19 mequiv. of $H^+$), dioxane (3 ml), and water (6 mg, 0.33 mmol) was stirred and heated at 40° C. under nitrogen for 8 hr. The mixture was cooled to 25° C. and filtered. The residue on the Buchner funnel was washed with dioxane and the filtrate was evaporated to dryness at reduced pressure. The residue which resulted after the dioxane evaporation was treated with water (10 ml), dichloromethane (20 ml), and enough 5% sodium bicarbonate to bring the pH to 8.5-9.0. The layers were separated, and the aqueous layer was re-extracted with dichloromethane (4×15 ml). The combined organic layer was dried and evaporated to dryness at 25° C. under vacuum to give a viscous oil. HPLC analysis showed about 30-35% of ethyl-hydroxymethyl-carbamic acid 3-R-prop-2-ynylamino-indan-5-yl ester free base.

Example 3f

Preparation of ethyl-hydroxymethyl-carbamic acid 3-S-(prop-2-ynylamino)-indan-5-yl ester The title compound is prepared using the starting material ethyl-carbamic acid 3-S-(N-Boc-prop-2-ynylamino)-indan-5-yl ester according to the procedures described in Examples 1-3e.

Example 4

Preparation of ethyl-hydroxymethyl-carbamic acid 3-R-(prop-2-ynylamino)-indan-5-yl ester fumarate (2:1)

Fumaric acid (0.49 g, 4.25 mmol, 0.5 eq) was added to a solution of ethyl-hydroxymethyl-carbamic acid 3-R-(prop-2-ynylamino)-indan-5-yl ester free base (2.45 g, 8.5 mmol) in iPrOH (49 ml), and the resulting suspension slightly warmed for a few seconds by a heat gun. A white suspension was formed, and the mixture was stirred at room temperature for 1 hr, and cooled in an ice bath for 30 min. The suspension was filtered, washed with cold iPrOH and dried under vacuum overnight to give the title compound as a white solid (2.45 g, 7.1 mmol, 83%), mp: 114-6° C.

Spectral and analytical data of ethyl-hydroxymethyl-carbamic acid 3-R-(prop-2-ynylamino)-indan-5-yl ester fumarate (2:1):

$^1$H-NMR ($D_2O$, δ):
Major Rotamer:
1.18 (brt, J=7 Hz, 3H, $MeCH_2$), 2.28 (m, 1H, H-2), 2.58 (m, 1H, H-2), 2.96 (ddd, J=16, 9, 4 Hz, 1H, H-1), 2.99 (t, J=2.5 Hz, 1H, $NCH_2CCH$), 3.12 (dt, J=16, 8 Hz, 1H, H-1), 3.43 (brq, J=7 Hz, 2H, $MeCH_2$), 3.93 (m, 2H, $NCH_2CCH$), 4.92 (dd, J=8, 3 Hz, 1H, H-3), 5.0 (brs, 2H, $NCH_2OH$), 6.44 (s, 2H, fumarate-CH), 7.16 (dd, J=8, 2 Hz, 1H, H-6), 7.28 (d, J=2 Hz, 1H, H-4), 7.40 (d, J=8 Hz, 1H, H-7) ppm.

Minor Rotamer:
1.27 (brt, J=7 Hz, 3H, $MeCH_2$), 2.28 (m, 1H, H-2), 2.58 (m, 1H, H-2), 2.96 (ddd, J=16, 9, 4 Hz, 1H, H-1), 2.99 (t, J=2.5 Hz, 1H, $NCH_2CCH$), 3.12 (dt, J=16, 8 Hz, 1H, H-1), 3.56 (brq, J=7 Hz, 2H, $MeCH_2$), 3.93 (m, 2H, $NCH_2CCH$), 4.87 (brs, 2H, $NCH_2OH$), 4.92 (dd, J=8, 3 Hz, 1H, H-3), 6.44 (s, 2H, fumarate-CH), 7.16 (dd, J=8, 2 Hz, 1H, H-6), 7.28 (d, J=2 Hz, 1H, H-4), 7.40 (d, J=8 Hz, 1H, H-7) ppm.

$^{13}$C-NMR ($D_2O$, δ):
Major Rotamer:
13.62 ($MeCH_2$), 29.51 (C-2), 29.81 (C-1), 34.89 ($NCH_2CCH$), 43.17 ($MeCH_2$), 62.23 (C-3), 71.46 ($NCH_2OH$), 73.86 ($NCH_2CCH$), 78.76 ($NCH_2CCH$), 119.52 (C-4), 124.52 (C-6), 127.19 (C-7), 135.93 (fumarate CH), 137.91 (C-3a), 143.72 (C-7a), 150.17 (C-5), 156.62 (NCO), 174.93 (fumarate $CO_2$).

Minor Rotamer
14.32 ($MeCH_2$), 29.51 (C-2), 29.81 (C-1), 34.89 ($NCH_2CCH$), 42.86 ($MeCH_2$), 62.23 (C-3), 71.71 ($NCH_2OH$), 73.86 ($NCH_2CCH$), 78.76 ($NCH_2CCH$), 119.52 (C-4), 124.52 (C-6), 127.19 (C-7), 135.93 (fumarate CH), 137.91 (C-3a), 143.72 (C-7a), 150.17 (C-5), 156.62 (NCO), 174.93 (fumarate $CO_2$) ppm.

MS: 289 ($MH^+$, 6), 234 (100), 216 (30), 133 (71).

Elemental analysis: calcd for $C_{32}H_{40}N_4O_6 \cdot C_4H_4O_4$: C, 62.42; H, 6.40; N, 8.09. found: C-62.30%, H-6.63%, N-7.85%.

Example 5

Preparation of carbonic acid 3-R-(N-Boc-amino)-indan-5-yl ester chloromethyl ester 3-R-(N-Boc-amino)-indan-5-ol was synthesized as described in U.S. Pat. No. 6,303,650, Column 6. A solution of 3-R-(N-Boc-amino)-indan-5-ol (15.0 g) and triethylamine (8.7 ml) in methylene chloride (60 ml) was added dropwise to a stirred and ice-cooled solution of chloromethyl chloroformate (8.16 g) in methylene chloride (20 ml). The mixture was stirred for 2 h at rt, washed with 5% $NaHCO_3$ solution and water, dried and evaporated to dryness. The residue was crystallized (toluene/hexane) to give 13.0 g (63.3%) of the title compound.

$^1$H NMR (DMSO-$d_6$, δ): 7.35 (d, 1H, NH), 7.30 (d, 1H, Ph), 7.08 (m, 2H, Ph), 6.0 (s, 2H, $CH_2Cl$), 4.95 (q, 1H, C3-H), 2.9-2.6 (m, 2H, C1), 2.35 (m, 1H, C2-H), 1.82 (m, 1H, C2-H'), 1.40 (s, 9H, tBu) ppm.

Example 6

Preparation of methyl-carbamic acid 3-R-(N-Boc-amino)-indan-5-yl ester

Carbonic acid 3-R-(N-Boc-amino)-indan-5-yl ester chloromethyl ester prepared in Example 5 (12.6 g) was combined with ethanolic methylamine (14 ml of a 33% solution) in dioxane (110 ml) and was stirred at rt for 3 h and evaporated to dryness. The residue was dissolved in EtOAc (200 ml), and the solution was filtered, washed with water, dried and evaporated to dryness. The residue was crystallized from EtOAc/ether to give the title compound (10.3 g, 91.1%).

$^1$H NMR (DMSO-$d_6$, δ): 7.60 (m, 1H, NHMe), 7.33 (d, 1H, NHBoc), 7.20 (d, 1H, Ph), 6.90 (m, 2H, Ph), 4.95 (q, 1H, C3-H), 2.9-2.6 (m, 2H, C1), 2.65 (d, 3H, Me), 2.35 (m, 1H, C2-H), 1.85 (m, 1H, C2-H'), 1.44 (s, 9H, tBu) ppm.

Example 7a

Preparation of methyl-carbamic acid 3-R-amino-indan-5-yl ester HCl

A 10% solution of HCl in EtOAc (150 ml) was added to a solution of methyl-carbamic acid 3-R-(N-Boc-amino)-indan-5-yl ester prepared in Example 6 (10.3 g) in EtOAc (220 ml). The suspension was stirred at rt for 15 min, and the solid collected by filtration (7.03 g, 86.3%).

$^1$H NMR (DMSO-d$_6$, δ): 8.75 (br s, 3H, NH$_3^+$), 7.70 (m, 1H, NHMe), 7.40 (s, 1H, Ph), 7.30 (d, 1H, Ph), 7.05 (d, 1H, Ph), 4.65 (br s, 1H, C3-H), 3.05 (m, 1H, C1-H), 2.80 (m, 1H, C1-H'), 2.65 (d, 3H, Me), 2.45 (m, 1H, C2-H), 2.05 (m, 1H, C2-H').

Example 7b

Preparation of methyl-carbamic acid 3-S-amino-indan-5-yl ester HCl

The title compound is prepared using the starting material 3-S-(N-Boc-amino)-indan-5-ol according to the procedures described in Examples 5-7a.

Example 8

Preparation of carbonic acid chloromethyl ester 3-R-(N-Boc-prop-2-ynylamino)-indan-5-yl ester 3-R-(N-Boc-prop-2-ynylamino)-indan-5-ol was prepared as described in PCT Application Publication No. WO 03/072055, FIG. 1. A solution of 3-R-(N-Boc-prop-2-ynylamino)-indan-5-ol (10.2 g) and triethylamine (3.74 g) in methylene chloride (30 ml) was added dropwise to a stirred and ice-cooled solution of chloromethyl chloroformate (4.8 g) in methylene chloride (35 ml). The mixture was stirred for 2 h at rt, washed with 5% NaHCO$_3$ solution and water, dried and evaporated to dryness to give 13.45 g (100%) of the title compound as an oil.

$^1$H NMR (DMSO-d$_6$, δ), mixture of two rotamers: 7.35 (d, 1H, Ph), 7.16 (d, 1H, Ph), 7.03 (s, 1H, Ph), 6.0 (s, 2H, CH$_2$Cl), 5.62, 5.20 (2m, 1H, C3-H), 4.16, 3.88 (2m, 2H, CH$_2$CCH), 3.1 (s, 1H, CC≡H), 3.0 (m, 1H, C1-H), 2.84 (m, 1H, C1-H'), 2.45 (m, 1H, C2-H), 2.19 (m, 1H, C2-H'), 1.50, 1.20 (2s, 9H, tBu) ppm.

Example 9

Preparation of methyl-carbamic acid 3-R-(N-Boc-prop-2-ynylamino)-indan-5-yl ester Carbonic acid chloromethyl ester 3-R-(N-Boc-prop-2-ynylamino)-indan-5-yl ester prepared in Example 8 (13.45 g) was combined with ethanolic methylamine (12.5 ml of a 33% solution) in dioxane (165 ml) and was stirred at rt for 2 h and evaporated to dryness. The residue was dissolved in EtOAc (200 ml), and the solution was filtered, washed with water, dried and evaporated to dryness. The residue was crystallized from ether/hexane to give the title compound (9.35 g, 77.3%).

$^1$H NMR (DMSO-d$_6$, δ), mixture of two rotamers: 7.55 (m, 1H, NH), 7.23 (d, 1H, Ph), 6.92 (d, 1H, Ph), 6.80 (s, 1H, Ph), 5.62, 5.20 (2m, 1H, C3-H), 4.16, 3.80 (2m, 2H, CH$_2$CCH), 3.1 (s, 1H, CCH), 2.95 (m, 1H, C1-H), 2.78 (m, 1H, C1-H'), 2.65 (d, 3H, Me), 2.40, (m, 1H, C2-H), 2.15 (m, 1H, C2-H'), 1.50, 1.20 (2s, 9H, tBu) ppm.

Example 10a

Preparation of methyl carbamic acid 3-R-(prop-2-ynylamino)-indan-5-yl ester HCl

A 10% solution of HCl in EtOAc (100 ml) was added to a solution of methyl-carbamic acid 3-R-(N-Boc-prop-2-ynylamino)-indan-5-yl ester prepared in Example 9 (9.0 g) in EtOAc (90 ml). The suspension was stirred at rt for 15 min, and the solid collected by filtration (7.3 g, 98.6%).

$^1$H NMR (DMSO-d$_6$, δ): 10.3 (br s, 3H, NH$_3^+$), 7.70 (m, 1H, NHMe), 7.50 (s, 1H, Ph), 7.30 (d, 1H, Ph), 7.05 (d, 1H, Ph), 4.80 (br s, 1H, C3-H), 3.95 (m, 2H, CH$_2$CCH), 3.75 (s, 1H, CC≡H), 3.10 (m, 1H, C1-H), 2.80 (m, 1H, C1-H'), 2.65 (d, 3H, Me), 2.45 (m, 1H, C2-H), 2.30 (m, 1H, C2-H').

Example 10b

Preparation of Methyl carbamic acid 3-S-(prop-2-ynylamino)-indan-5-yl ester HCl

Methyl carbamic acid 3-S-(prop-2-ynylamino)-indan-5-yl ester HCl was prepared from 3-S-(N-Boc-prop-2-ynylamino)-indan-5-ol according to the procedures described in Examples 8-10a.

In Vitro Studies

Example 11

Inhibition of MAO Activity In Vitro

The MAO enzyme source was a homogenate of rat brain in 0.3M sucrose. The homogenate was diluted appropriately, and pre-incubated with serial dilutions of test compounds—diluted in phosphate buffer containing clogyline when 2-phenylethylamine (PEA) is the substrate, and diluted in phosphate buffer containing selegiline when 5-hydroxytryptamine (5-HT) is the substrate—for 60 minutes at 37° C. $_{14}$C-Labeled substrates (PEA for MAO-B determination and 5-HT for MAO-A determination) were then added, and the incubation continued for a further 20 minutes (PEA) or 30 minutes (5-HT). Substrate concentrations used were 10 μM (PEA) and 100 uM (5-HT). Enzyme concentration was chosen so that not more than 10% of the substrate was metabolized during the course of the reaction. Deaminated products were extracted into toluene-ethyl acetate (1:1 v/v) containing 0.4% (w/v) 2,5-diphenyloxazole (ppo) prior to determination by liquid scintillation counting. Radioactivity in the eluate indicated the production of neutral and acidic metabolites formed as a result of MAO activity. Activity of MAO in the sample was expressed as a percentage of control activity in the absence of inhibitor after subtraction of appropriate blank values. The activity determined using PEA as substrate is referred to as MAO-B, and that determined using 5-HT as MAO-A.

The experiment was performed using three inhibitors: Ethyl-hydroxymethyl-carbamic acid 3-R-(prop-2-ynylamino)-indan-5-yl ester fumarate (2:1) ("R—HCPAI"), Methyl-carbamic acid 3-R-(prop-2-ynylamino)-indan-5-yl ester hydrochloride ("R-MCPAI"), and Methyl-carbamic acid 3-R-amino-indan-5-yl ester hydrochloride ("R-MCAI").

Concentrations of each inhibitor producing 50% inhibition of substrate metabolism (IC$_{50}$) were calculated from the inhibition curves, and are shown in Table 1.

TABLE 1

| Inhibitor | IC$_{50}$ for MAO-A inhibition (µM) | IC$_{50}$ for MAO-B inhibition (µM) |
|---|---|---|
| R-MCPAI | 37 | 42 |
| R-MCAI | 32.2 | >1000 |
| R-HCPAI | 414 | 599 |

Example 12a

Inhibition of Acetylcholinesterase (AChE) Activity In Vitro

Enzyme and Reagents

Recombinant human AChE (C-1682), acetylthiocholine iodide (AcTh, A5771), bovine serum albumin (BSA, A-2153), and 5,5'-dithiobis(2-nitrobenzoic acid) (DTNB, D8130) were obtained from Sigma-Aldrich Israel. AChE was found to be in a tetrameric form by sucrose gradient. AChE was dissolved in phosphate buffer pH 8.0 containing 0.01% sodium azide NaAz and 1 mM EDTA and diluted to give a concentration of 15 units/ml. This solution was divided into aliquots of 0.5 ml, which were stored at −70° C. until use.

Enzyme Inhibition

The inhibitory activity against AChE was determined by the method of Ellmann et al. (Biochemical Pharmacology, 1961 (7) 88-95) using AcTh as a substrate. To characterize the carbamoylation step, a traditional stopped time assay was performed, in which AChE was incubated at 37° C. with a minimum of 5 different concentrations of inhibitor in the assay buffer, and aliquots were transferred to an ELISA multiscan microplate reader (Labsystems) at various times for the determination of residual AChE activity, with Ascent PC software. The rate of reaction was measured at 412λ at 37° C. in 0.2 ml wells containing AChE 0.023 units per ml, DTNB 0.4-0.5 mM, AcTh 0.50 or 1 mM and BSA (0.05%) in 50 mM phosphate buffer as described above. Measurements were made every 5 min for up to 5 hours.

The experiment was performed using three inhibitors: Ethyl-hydroxymethyl-carbamic acid 3-R-(prop-2-ynylamino)-indan-5-yl ester fumarate (2:1) ("R—HCPAI"), Methyl-carbamic acid 3-R-(prop-2-ynylamino)-indan-5-yl ester hydrochloride ("R-MCPAI"), and Methyl-carbamic acid 3-R-amino-indan-5-yl ester hydrochloride ("R-MCAI").

The inhibition of AChE by carbamates involves the formation of a reversible complex (EOH•CX), followed by carbamoylation of the enzyme to form (EOC) and a leaving group (HX). The carbamoylated enzyme is then hydrolyzed by water to regenerate the free enzyme (EOH).

The formation of the reversible complex is represented by the equilibrium constant: $K_D$. For the carbamoylation phase of the inhibition process the unimolecular rate constant is represented by $k_{max}$, and the bimolecular rate constant by $k_i$.

TABLE 2

| Inhibitor | $k_{max}$ (min$^{-1}$) | $k_i$ (mM*min$^{-1}$) | $K_D$ (mM) |
|---|---|---|---|
| R-MCPAI | 0.435 | 13.00 ± 0.91 | 0.034 |
| R-MCAI | 1.63 | 76.9 ± 4.7 | 0.021 |
| R-HCPAI | 0.033 | 0.106 ± 0.008 | 0.306 |

This experiment shows that R-MCPAI and R-MCAI are potent inhibitors of acetylcholinesterase.

This experiment also shows that R-HCPAI is a weak inhibitor of acetylcholinesterase.

Example 12b

Inhibition of Butyrylcholinesterase (BuChE) Activity In Vitro

Enzyme and Reagents

BuChE from human serum (C-9971), butyrylthiocholine iodide (BuTh, B3253), bovine serum albumin (BSA, A-2153) 5,5'-dithiobis(2-nitrobenzoic acid) (DTNB, D8130) were obtained from Sigma-Aldrich Israel. BuChE was dissolved in phosphate buffer pH 8.0 containing 0.01% sodium azide (NaAz) and 1 mM EDTA and diluted to give a concentration of 35.9 units/ml. This solution was divided into aliquots of 0.5 ml, which were stored at −70° C. until use.

Enzyme Inhibition

The inhibitory activity against BuChE was determined by the method of Ellmann et al. (Biochemical Pharmacology, 1961 (7) 88-95) using BuTh as a substrate. To characterize the carbamoylation step, a traditional stopped time assay was performed, in which BuChE was incubated at 37° C. with a minimum of 5 different concentrations of inhibitor in the assay buffer, and aliquots were transferred to an ELISA multiscan microplate reader (Labsystems) at various times for the determination of residual BuChE activity, with Ascent PC® software. The rate of reaction was measured at 412λ at 37° C. in 0.2 ml wells containing AChE 0.023 units per ml, DTNB 0.4-0.5 mM, AcTh 0.50 or 1 mM and BSA (0.05%) in 50 mM phosphate buffer as described above. For all compounds measurements were made every 2 min for 15 min and then every 15 min for 3 hr.

The experiment was performed using three inhibitors: Ethyl-hydroxymethyl-carbamic acid 3-R-(prop-2-ynylamino)-indan-5-yl ester fumarate (2:1) ("R—HCPAI"), Methyl-carbamic acid 3-R-(prop-2-ynylamino)-indan-5-yl ester hydrochloride ("R-MCPAI"), and Methyl-carbamic acid 3-R-amino-indan-5-yl ester ("R-MCAI") hydrochloride.

The inhibition of BuChE by carbamates involves the formation of a reversible complex (EOH•CX), followed by carbamoylation of the enzyme to form (EOC) and a leaving group (HX). The carbamoylated enzyme is then hydrolyzed by water to regenerate the free enzyme (EOH). The formation of the reversible complex is represented by the equilibrium constant: $K_D$. For the carbamoylation phase of the inhibition process the unimolecular rate constant is represented by $k_{max}$, and the bimolecular rate constant by $k_i$.

TABLE 3

| Inhibitor | $k_{max}$ (min$^{-1}$) | $k_i$ (mM*min$^{-1}$) | $K_D$ (mM) |
|---|---|---|---|
| R-MCPAI | 0.65 ± 0.03 | 31.3 ± 2.0 | 0.021 ± 0.002 |
| R-MCAI | 0.516 ± 0.050 | 14.5 ± 0.42 | 0.036 ± 0.005 |
| R-HCPAI | 0.104 ± 0.043 | 0.936 ± 0.06 | 0.111 ± 0.05 |

This experiment shows that R-MCPAI and R-MCAI are potent inhibitors of butyrylcholinesterase.

This experiment also shows that R—HCPAI is a weak inhibitor of butyrylcholinesterase.

Example 13

Use of synthetic ethyl-hydroxymethyl-carbamic acid 3-R-(prop-2-ynylamino)-indan-5-yl ester fumarate (2:1) as a reference standard for assay determination of ethyl-hydroxymethyl-carbamic acid 3-R-(prop-2-ynylamino)-indan-5-yl ester in biological samples The objective of the method is the detection of ladostigil and its known metabolite ethyl-hydroxymethyl-carbamic acid 3-R-(prop-2-ynylamino)-indan-5-yl ester in plasma. The method consists of solid phase extraction (SPE) with both manual and automatic options for sample preparation and LC-MS/MS analysis. Ethyl-hydroxymethyl-carbamic acid 3-R-(prop-2-ynylamino)-indan-5-yl ester in plasma is quantified using ethyl-hydroxymethyl-carbamic acid 3-R-(prop-2-ynylamino)-indan-5-yl ester fumarate 2:1 analytical standard and its own isotopic internal standard ($^{13}$C-ethyl-hydroxymethyl-carbamic acid 3-(prop-2-ynylamino)-indan-5-yl ester fumarate (2:1).

LC-MS/MS Conditions

LC-MS/MS analyses is carried out using a Perkin Elmer Sciex API 2000 mass spectrometer, which is connected to the HPLC system via a TIS interface operated at 350° C. The mass spectrometer is programmed to admit the protonated molecules [M+H]+ via the first quadropole filter (Q1), with collision-induced fragmentation at Q2. The product ion is monitored via Q3. The precursor and product ions are 289 and 133, respectively.

The LC conditions include Waters Symmetry C18 3.5µ 2.1×50 mm column with Pre-column Filter 1/16", Peek, 2 µm and mobile phase composition of acetonitrile, 0.1% formic acid and 1% THF in water in gradient mode up to 40% of acetonitrile content.

Sample Preparation

Plasma sample is spiked with Internal Standard, then centrifuged and the supernatant is diluted with 2% cc NH$_4$OH and 5% methanol in water (Solvent B). The volume of the sample is loaded on a STRATA X 33µ Polymeric Sorbent 30 mg/1 mL Extraction Cartridge, which is pre-conditioned first with methanol (Solvent A) and then with Solvent B. The cartridge is washed with Solvent B and sample is eluted with 2% glacial Acetic acid and 80% methanol in water (Solvent C). The eluted sample is evaporated at about 37° C. to dryness and reconstituted with 0.1% formic acid and 1% THF in water. The sample is then filtered through 0.2µ filter before injection into LC-MS/MS.

Quantification

The amount of ethyl-hydroxymethyl-carbamic acid 3-R-(prop-2-ynylamino)-indan-5-yl ester in plasma sample is quantified vs. plasma calibration curve of ethyl-hydroxymethyl-carbamic acid 3-R-(prop-2-ynylamino)-indan-5-yl ester and using its own isotopic internal standard.

Conclusion

Ethyl-hydroxymethyl-carbamic acid 3-R-(prop-2-ynylamino)-indan-5-yl ester has been found to be a metabolite of ladostigil in vivo. It can be used as a reference standard or marker in investigating the pharmacokinetics and metabolic profile of ladostigil.

In Vivo Studies

Example 14

Chronic administration of ethyl-hydroxymethyl-carbamic acid 3-R-(prop-2-ynylamino)-indan-5-yl ester fumarate (2:1) and ladostigil tartrate to rats 30 rats were separated randomly into 5 testing groups of 6 rats each. Group 1 was the control group to which no drug was administered. Ethyl-hydroxymethyl-carbamic acid 3-R-(prop-2-ynylamino)-indan-5-yl ester fumarate (2:1) was administered to groups 2, 3, 4 in dosages of 150, 75, and 37.5 µmol/kg respectively, daily, perorally ("P.O.") for seven consecutive days. Water was used as a vehicle.

Rats were sacrificed, out of sight of the other rats, 2 hours after the last administration. Brains were removed into Petri dishes on ice, the cerebellums were rolled out, and the brains cut into halves for analysis. Livers and intestines were removed for MAO determination. Organs were homogenated for enzyme inhibition analysis.

The MAO inhibition after administration of ethyl-hydroxymethyl-carbamic acid 3-R-(prop-2-ynylamino)-indan-5-yl ester fumarate (2:1) in various organs is listed in Table 4 calculated in percent relative to the control group.

TABLE 4

| Dose in | Brain | | Liver | | Duodenum | |
| --- | --- | --- | --- | --- | --- | --- |
| µmol/kg | MAO-A | MAO-B | MAO-A | MAO-B | MAO-A | MAO-B |
| 150 | 72 | 83 | 16 | 34 | 21 | 35 |
| 75 | 41 | 62 | 9 | 18 | 18 | 31 |
| 37.5 | 8 | 17 | 3 | 15 | −25 | 7 |

The data indicates that administration of ethyl hydroxymethyl-carbamic acid 3-R-(prop-2-ynylamino)-indan-5-yl ester fumarate (2:1) causes brain-selective MAO inhibition.

Example 15

Administration of Ladostigil Tartrate Tablets to Humans

Tablets were prepared through wet granulation using isopropanol. The tablets were made with the excipients listed in Table 5:

TABLE 5

| Excipient | Tablet equivalent to 20 mg ladostigil tartrate base | Tablet equivalent to 50 mg ladostigil tartrate base | Tablet equivalent to 80 mg ladostigil tartrate base | Function |
| --- | --- | --- | --- | --- |
| Ladostigil tartrate | 25.6 | 64.0 | 102.4 | Drug Substance |
| Mannitol USP/BP | 13.4 | 33.5 | 53.6 | Filler |
| Pregelatinized starch (starch 1500 NF) | 32.0 | 80.0 | 128.0 | Disintegrant |
| Syloid 244 (Colloidal Silicon Dioxide) | 1.8 | 4.5 | 7.2 | Disintegrant and flowing agent |
| Polividone 30 (PVP) | 7.2 | 18.0 | 28.8 | Binder |

TABLE 5-continued

| Excipient | Tablet equivalent to 20 mg ladostigil tartrate base | Tablet equivalent to 50 mg ladostigil tartrate base | Tablet equivalent to 80 mg ladostigil tartrate base | Function |
|---|---|---|---|---|
| Mannitol granulate | 120.0 | — | — | Filler |
| Stearic acid | 4.0 | 4.0 | 6.4 | Lubricant |
| Talc | 8.0 | 8.0 | 12.8 | Lubricant |
| Isopropyl alcohol | q.s. | q.s. | q.s. | |
| Total tablet weight | 212.0 | 212.0 | 339.2 | |

Administration of Ladostigil Tartrate to Alzheimer's Disease Patients 8 patients, 7 female and 1 male, ages 62-81 with a median age of 68 and above with diagnosis of probable Alzheimer's disease according to DSM-IV (290.00 or 290.10) and NINCDS-ADRDA criteria were administered ladostigil tartrate according to the following schedule:

Week 1: 70 mg (50+20) once daily.
Week 2: 70 mg (50+20) twice daily.
Week 3-Week 9: 100 mg (50*2) twice daily.

4 patients (3 male and 1 female) aged 70 to 84 years old were in the placebo group.

Pharmacokinetic Analysis

Pharmacokinetic analysis was performed on Week 4 (maintenance analysis) and on Week 9 (termination analysis). At maintenance analysis, samples were collected pre-dose and at 0.25, 0.5, 1, 2, and 3 hours post-dose. At termination analysis, samples were collected pre-dose and at 0.25, 0.5, 1, 2, 3, 4 and 6 hours post-dose.

Mean $C_{max}$ after dosing and mean $C_{min}$ (concentration at pre-dose) of ladostigil tartrate and 3 of its metabolites at maintenance analysis (M) and at termination analysis (T) were determined and are listed in Table 6, as well as half life ($t_{1/2}$) at termination. The concentration measurements are expressed in nmol/ml and the $t_{1/2}$ is expressed in terms of hours.

TABLE 7

| Analyte | $C_{min}$ (M) | $C_{min}$ (T) | $C_{max}$ (M) | $C_{max}$ (T) | $t_{1/2}$ |
|---|---|---|---|---|---|
| R-CPAI | 0.0164 | 0.0109 | 2.02 | 1.88 | 1.08 |
| R-HCPAI | 0.0232 | 0.0137 | 3.63 | 3.30 | 1.03 |
| R-MCPAI | 0.0174 | 0.0132 | 1.29 | 1.07 | 1.39 |
| R-MCAI | 0.153 | 0.139 | 0.270 | 0.261 | 8.09 |

MAO-B Inhibition

Monoamine oxidase B inhibition in plasma samples from the aforementioned patients was determined at baseline and at termination analysis (see Example 11, supra, for determination of MAO B inhibition in samples). The percent inhibi-

TABLE 6[1]

| | Patient Number | | | | | | | |
|---|---|---|---|---|---|---|---|---|
| | 1 | 2 | 3 | 4 | 5 | 6 | 7 | 8 |
| MAO (T) (%) | −55 | −85 | −98 | −76 | −89 | −76 | −54 | −64 |
| DHPG (T) (%) | −63 | −86 | ND | ND | >−79 | −73 | −30 | −13 |
| AUC (ng * hr/mL) | | | | | | | | |
| ladostigil (M) | 314 | 589 | 1005 | 927 | 436 | 551 | 52 | 500 |
| ladostigil (T) | 246 | 2305 | 1449 | 482 | 398 | 901 | 118 | 350 |
| MCPAI (M) | 684 | 103 | 596 | 764 | 491 | 630 | 212 | 304 |
| MCPAI (T) | 493 | 789 | 621 | 487 | 551 | 947 | 584 | 343 |
| MCAI (M) | 62 | 121 | 172 | 191 | 171 | 144 | 213 | 86 |
| MCAI (T) | 570 | 733 | 958 | 672 | 895 | 964 | 186 | 426 |
| HCPAI (M) | 1662 | 600 | 2287 | 2152 | 1702 | 1891 | 519 | 1513 |
| HCPAI (T) | 1295 | 3101 | 2520 | 1744 | 1651 | 2399 | 1037 | 1337 |
| $C_{max}$ (nmol/mL) | | | | | | | | |
| ladostigil (M) | 1.1 | 1.2 | 3.5 | 3.9 | 1.4 | 1.5 | 0.2 | 1.7 |
| ladostigil (T) | 0.7 | 3.8 | 3.9 | 1.6 | 1.0 | 2.5 | 0.4 | 1.3 |
| MCPAI (M) | 1.8 | 0.3 | 1.2 | 3.0 | 1.5 | 1.3 | 0.5 | 0.7 |
| MCPAI (T) | 1.3 | 1.0 | 1.0 | 1.1 | 1.3 | 1.3 | 1.0 | 0.6 |
| MCAI (M) | 0.1 | 0.2 | 0.3 | 0.3 | 0.3 | 0.3 | 0.4 | 0.2 |
| MCAI (T) | 0.2 | 0.2 | 0.3 | 0.2 | 0.4 | 0.3 | 0.2 | 0.2 |
| HCPAI (M) | 3.6 | 1.5 | 3.7 | 7.0 | 4.7 | 4.0 | 1.2 | 3.3 |
| HCPAI (T) | 3.2 | 3.9 | 3.9 | 3.9 | 3.7 | 3.2 | 2.1 | 2.6 |

[1] R-CPAI = ladostigil;

HCPAI=R-HCPAI=Ethyl-hydroxymethyl-carbamic acid 3-R-(prop-2-ynylamino)-indan-5-yl ester;
MCPAI=R-MCPAI=Methyl-carbamic acid 3-R-(prop-2-ynylamino)-indan-5-yl ester; and
MCAI=R-MCAI=Methyl-carbamic acid 3-R-amino-indan-5-yl ester.

tion was calculated for each patient, and the mean percent inhibition was then determined to be 75% (standard deviation=16) at the termination analysis.

HPLC Analysis of MAO-A Inhibition

Decrease of 3,4-dihydroxyphenylglycol ("DHPG") in plasma is indicative of monoamine oxidase inhibition, especially in the brain. DHPG plasma concentrations were measured in 6 of the aforementioned patients at baseline and at termination analysis, using HPLC equipped with an electrochemical detector.

The decrease in DHPG concentration in the six patients was determined. The average decrease in DHPG concentration was determined to be 57% with a standard deviation of 29.

Discussion

The data show that the analytes were present at pre-dose (which corresponds to 12 hours after the previous dose) both at maintenance and at termination analyses.

There is evidence of significant MAO-B inhibition.

Cholinesterase inhibition at pre-dose administration both at maintenance and at termination analyses was also evident.

What is claimed is:

1. A method for treating an individual who has been identified as having Alzheimer's disease which comprises administering orally to the individual a therapeutically effective amount of ladostigil or a pharmaceutically active salt thereof, wherein the therapeutically effective amount is selected from the group consisting of: 70 mg per day, 140 mg per day, and 200 mg per day.

2. The method of claim 1 wherein the therapeutically effective amount is 200 mg per day.

3. The method of claim 1 wherein the therapeutically effective amount is 200 mg per day administered in two 100 mg doses per day.

4. The method of claim 1 wherein the therapeutically effective amount is 140 mg per day.

5. The method of claim 1 wherein said therapeutically effective amount is 140 mg per day administered in two 70 mg doses per day.

6. The method of claim 1 wherein a pharmaceutically active salt of ladostigil is administered in a unit dosage form with the salt present in the therapeutically effective amount.

7. The method of claim 1 wherein a pharmaceutically active salt of ladostigil is ladostigil tartrate.

8. A method for treating an individual who has been identified as having Alzheimer's disease which comprises administering orally to the individual a therapeutically effective amount of a pharmaceutically active salt of ladostigil, wherein the therapeutically effective amount of the ladostigil salt is one that is equivalent to a dose of ladostigil that is selected from the group consisting of: 70 mg per day, 140 mg per day and 200 mg per day.

9. The method of claim 8, wherein the pharmaceutically active salt of ladostigil is ladostigil tartrate and is administered in a single dose that is equivalent to a dose of 70 mg per day, 140 mg per day or 200 mg per day of ladostigil or in two doses that are equivalent to doses of 35, 70 or 100 mg of ladostigil.

10. The method of claim 8, wherein the pharmaceutically active salt of ladostigil is ladostigil tartrate and is administered in a single dose that is equivalent to a dose of 70 mg per day or 140 mg per day of ladostigil or in two doses of 70 mg of ladostigil.

* * * * *